(12) United States Patent
Kikuchi et al.

(10) Patent No.: US 7,252,972 B2
(45) Date of Patent: Aug. 7, 2007

(54) METHODS FOR SECRETORY PRODUCTION OF PROTEINS

(75) Inventors: Yoshimi Kikuchi, Kawasaki (JP); Masayo Date, Kawasaki (JP); Yukiko Umezawa, Kawasaki (JP); Keiichi Yokoyama, Kawasaki (JP); Haruo Heima, Kawasaki (JP); Hiroshi Matsui, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 417 days.

(21) Appl. No.: 10/673,860

(22) Filed: Sep. 30, 2003

(65) Prior Publication Data

US 2004/0126847 A1 Jul. 1, 2004

Related U.S. Application Data

(63) Continuation of application No. PCT/JP02/02978, filed on Mar. 27, 2002.

(30) Foreign Application Priority Data

Mar. 30, 2001 (JP) .............................. 2001-098808

(51) Int. Cl.
*C12P 21/04* (2006.01)
*C12N 1/21* (2006.01)

(52) U.S. Cl. ................ 435/69.8; 435/252.32

(58) Field of Classification Search ............... 435/69.1, 435/476, 487, 320.1, 252.32
See application file for complete search history.

(56) References Cited

U.S. PATENT DOCUMENTS

| | | | |
|---|---|---|---|
| 4,822,738 A | 4/1989 | Miwa et al. | 435/252.3 |
| 4,965,197 A | 10/1990 | Liebl et al. | 435/69.8 |
| 5,547,864 A | 8/1996 | Kawasaki et al. | 435/170 |
| 5,643,790 A | 7/1997 | Morinaga et al. | |
| 6,027,920 A | 2/2000 | Joliff et al. | 435/69.7 |
| 6,090,607 A | 7/2000 | Van Den Broek et al. | 435/223 |

FOREIGN PATENT DOCUMENTS

| | | |
|---|---|---|
| JP | 10108675 | 4/1998 |
| JP | 11169182 | 6/1999 |
| WO | WO88/09821 | 12/1988 |
| WO | WO93/03158 | 2/1993 |
| WO | WO01/23591 | 4/2001 |

OTHER PUBLICATIONS

Helen Billman-Jacobe et al., Expression and Secretion of Heterologous Proteases by *Corynebacterium glutamicum*, Journal of Bacteriology, Mar. 1992, p. 1854-1861, vol. 174, No. 6.
Wolfgang Liebl et al., Expression, Secretion, and Processing of Staphylococcal Nuclease by *Corynebacterium glutamicum*, Applied and Environmental Microbiology, Apr. 1995, p. 1610-1613, vol. 61, No. 4.
K. Salim et al., Heterologous Expression of the Mycobacterium tuberculosis Gene Encoding Antigen 85A in *Corynebacterium glutamicum*, Applied and Environmental Microbiology, Nov. 1997, p. 4392-4400, vol. 63, No. 11.
Kinya Washizu et al., Molecular Cloning of the Gene for Microbial Transglutaminase from *Streptoverticillium* and Its Expression in *Streptomyces lividans*, Biosci. Biotech. Biochem., 58(1), 82-87, 1994.
Shino Takihana et al., Chemical Synthesis of the Gene for Microbial Transglutaminase from *Streptoverticillium* and Its Expression in *Escherichia coli*, Biotech. Biochem., 58(1), 88-92, 1994.
R Duran et al., Purification, characterization, and gene cloning of transglutaminase from *Streptoverticillium*.
Int'l Search Report, Jun. 25, 2002, Japan Patent Office.
Int'l Preliminary Examination Report, Nov. 26, 2002, Japan Patent Office.
Ralf Pasternack et al., Bacterial pro-transglutaminase from *Streptoverticillium mobaraense* Purification, characterization and sequence of the zymogen, Eur. J. Biochem. 257, 570-576 (1998).
J. L. Peyret et al, Characterization of the cspB gene encoding PS2, an ordered surface-layer protein in *Corynebacterium glutamicum*, Molecular Microbiology (1993) 9(1), 97-109.
U.S. Appl. No. 10/149,450, filed Jun. 27, 2002, Nakanishi et al.

*Primary Examiner*—Nancy Vogel
(74) *Attorney, Agent, or Firm*—Cermak & Kenealy, LLP; Shelly Guest Cermak

(57) ABSTRACT

The object of the present invention is to provide a method of producing a heterologous protein by making a coryneform bacterium to produce and efficiently extracellularly secrete (secreto-production) an industrially useful heterologous protein. According to the present invention, a genetic construct is used where a gene sequence encoding an intended protein which is ligated to the downstream of a sequence encoding the signal peptide derived from a coryneform bacterium, the gene construct is introduced into a mutant coryneform bacterium which has a capacity of secreting the heterologous protein at least 2-fold higher than the wild type *Corynebacterium glutamicum* ATCC 13869, the mutant coryneform bacterium is cultured and the extracellularly released heterologous protein is recovered.

7 Claims, No Drawings

SEQUENCE LISTING

<160> NUMBER OF SEQ ID NOS: 60

<210> SEQ ID NO 1
<211> LENGTH: 43
<212> TYPE: PRT
<213> ORGANISM: Corynebacterium glutamicum

<400> SEQUENCE: 1

```
Met Arg Asp Thr Ala Phe Arg Ser Ile Lys Ala Lys Ala Gln Ala Lys
 1               5                  10                  15

Arg Arg Ser Leu Trp Ile Ala Ala Gly Ala Val Pro Thr Ala Ile Ala
             20                  25                  30

Leu Thr Met Ser Leu Ala Pro Met Ala Ser Ala
         35                  40

<210> SEQ ID NO 2
<211> LENGTH: 30
<212> TYPE: PRT
<213> ORGANISM: Corynebacterium glutamicum

<400> SEQUENCE: 2

Met Phe Asn Asn Arg Ile Arg Thr Ala Ala Leu Ala Gly Ala Ile Ala
 1               5                  10                  15

Ile Ser Thr Ala Ala Ser Gly Val Ala Ile Pro Ala Phe Ala
             20                  25                  30

<210> SEQ ID NO 3
<211> LENGTH: 25
<212> TYPE: PRT
<213> ORGANISM: Corynebacterium ammoniagenes

<400> SEQUENCE: 3

Met Lys Arg Met Lys Ser Leu Ala Ala Ala Leu Thr Val Ala Gly Ala
 1               5                  10                  15

Met Leu Ala Ala Pro Val Ala Thr Ala
             20                  25

<210> SEQ ID NO 4
<211> LENGTH: 782
<212> TYPE: DNA
<213> ORGANISM: Corynebacterium glutamicum
<220> FEATURE:
<221> NAME/KEY: CDS
<222> LOCATION: (579)..(782)

<400> SEQUENCE: 4
```

| | |
|---|---|
| aaattcctgt gaattagctg atttagtact tttcggaggt gtctattctt accaaatcgt | 60 |
| caagttgtgg gtagagtcac ctgaatatta attgcaccgc acgggtgata tatgcttatt | 120 |
| tgctcaagta gttcgaggtt aagtgtattt taggtgaaca aatttcagct tcgggtagaa | 180 |
| gactttcgat gcgcttcaga gcttctattg ggaaatctga caccacttga ttaaatagcc | 240 |
| taccccgaa ttgggggatt ggtcattttt tgctgtgaag gtagttttga tgcatatgac | 300 |
| ctgcgtttat aaagaaatgt aaacgtgatc agatcgatat aaaagaaaca gtttgtactc | 360 |
| aggtttgaag cattttctcc gattcgcctg gcaaaaatct caattgtcgc ttacagtttt | 420 |
| tctcaacgac aggctgctaa gctgctagtt cggtggccta gtgagtggcg tttacttgga | 480 |
| taaaagtaat cccatgtcgt gatcagccat tttgggttgt ttccatagca atccaaaggt | 540 |
| ttcgtctttc gataacctatt caaggagcct tcgcctct atg ttt aac aac cgt atc | 596 |
|                                             Met Phe Asn Asn Arg Ile |
|                                              1               5 |
| cgc act gca gct ctc gct ggt gca atc gca atc tcc acc gca gct tcc | 644 |
| Arg Thr Ala Ala Leu Ala Gly Ala Ile Ala Ile Ser Thr Ala Ala Ser | |
|             10                  15                  20 | |
| ggc gta gct atc cca gca ttc gct cag gag acc aac cca acc ttc aac | 692 |
| Gly Val Ala Ile Pro Ala Phe Ala Gln Glu Thr Asn Pro Thr Phe Asn | |
|         25                  30                  35 | |

```
atc aac aac ggc ttc aac gat gct gat gga tcc acc atc cag cca gtt     740
Ile Asn Asn Gly Phe Asn Asp Ala Asp Gly Ser Thr Ile Gln Pro Val
     40                  45                  50 gag cca gtt aac cac acc gag gaa acc ctc cgc gac ctg act             782
Glu Pro Val Asn His Thr Glu Glu Thr Leu Arg Asp Leu Thr
 55                  60                  65
```

<210> SEQ ID NO 5
<211> LENGTH: 68
<212> TYPE: PRT
<213> ORGANISM: Corynebacterium glutamicum

<400> SEQUENCE: 5

```
Met Phe Asn Asn Arg Ile Arg Thr Ala Ala Leu Ala Gly Ala Ile Ala
 1               5                  10                  15

Ile Ser Thr Ala Ala Ser Gly Val Ala Ile Pro Ala Phe Ala Gln Glu
             20                  25                  30

Thr Asn Pro Thr Phe Asn Ile Asn Asn Gly Phe Asn Asp Ala Asp Gly
         35                  40                  45

Ser Thr Ile Gln Pro Val Glu Pro Val Asn His Thr Glu Glu Thr Leu
     50                  55                  60

Arg Asp Leu Thr
 65
```

<210> SEQ ID NO 6
<211> LENGTH: 1809
<212> TYPE: DNA
<213> ORGANISM: Streptoverticillium mobaraense
<220> FEATURE:
<221> NAME/KEY: CDS
<222> LOCATION: (578)..(1798)

<400> SEQUENCE: 6

```
gtcgacgcgg gccgggaggg ggtgcggcgg cgcccttcgg ctgtgtggac gaagcgtcgg      60
gtcggagggg cggccggata tcgtccttgg ggcggggtgg ccggaattgc cgccatggtg     120
ttgccgggga atcgacccga agacatgatc acttctcgta tccacccgat cacgtatccg     180
ggagtcgaga agtgttacgc cgtgcccctg tccgcgtcct caccctgtc gccgtgacag      240 cgacccgcgt tcttccactc gcacggacgg ccccacagga cctttcggcc cgggctcgcc     300
ccgccgcctc ggtgacggcc tccgaataac gcggccgccg gggcctcggc cggttgaccg     360
atccgggtca cgcgcccgc cgggcgggcg gccacgtccg gtctcgcccc gcccgacatc      420
ggctgcgact gccttcgctc gcacttcttc ccgcctcccg gccgcgtttt tccgccgccg     480
aaggtgcggc gacgcgtacc gaatcccct tcatcgcgac gtgcttccgc acggccgcgt     540
tcaacgatgt tccacgacaa aggagttgca ggtttcc atg cgc ata cgc cgg aga     595
                                          Met Arg Ile Arg Arg Arg
                                            1               5 gct ctc gtc ttc gcc act atg agt gcg gtg tta tgc acc gcc gga ttc     643
Ala Leu Val Phe Ala Thr Met Ser Ala Val Leu Cys Thr Ala Gly Phe
         10                  15                  20 atg ccg tcg gcc ggc gag gcc gcc gcc gac aat ggc gcg ggg gaa gag     691
Met Pro Ser Ala Gly Glu Ala Ala Ala Asp Asn Gly Ala Gly Glu Glu
     25                  30                  35 acg aag tcc tac gcc gaa acc tac cgc ctc acg gcg gat gac gtc gcg     739
Thr Lys Ser Tyr Ala Glu Thr Tyr Arg Leu Thr Ala Asp Asp Val Ala
 40                  45                  50 aac atc aac gcg ctc aac gaa agc gct ccg gcc gct tcg agc gcc ggc     787
Asn Ile Asn Ala Leu Asn Glu Ser Ala Pro Ala Ala Ser Ser Ala Gly
 55                  60                  65                  70
```

-continued

| | |
|---|---|
| ccg tcg ttc cgg gcc ccc gac tcc gac gac agg gtc acc cct ccc gcc<br>Pro Ser Phe Arg Ala Pro Asp Ser Asp Asp Arg Val Thr Pro Pro Ala<br>75                          80                       85 | 835 |
| gag ccg ctc gac agg atg ccc gac ccg tac cgt ccc tcg tac ggc agg<br>Glu Pro Leu Asp Arg Met Pro Asp Pro Tyr Arg Pro Ser Tyr Gly Arg<br>90                          95                       100 | 883 |
| gcc gag acg gtc gtc aac aac tac ata cgc aag tgg cag cag gtc tac<br>Ala Glu Thr Val Val Asn Asn Tyr Ile Arg Lys Trp Gln Gln Val Tyr<br>105                        110                       115 | 931 |
| agc cac cgc gac ggc agg aag cag cag atg acc gag gag cag cgg gag<br>Ser His Arg Asp Gly Arg Lys Gln Gln Met Thr Glu Glu Gln Arg Glu<br>120                        125                       130 | 979 |
| tgg ctg tcc tac ggc tgc gtc ggt gtc acc tgg gtc aat tcg ggt cag<br>Trp Leu Ser Tyr Gly Cys Val Gly Val Thr Trp Val Asn Ser Gly Gln<br>135                        140                       145                       150 | 1027 |
| tac ccg acg aac aga ctg gcc ttc gcg tcc ttc gac gag gac agg ttc<br>Tyr Pro Thr Asn Arg Leu Ala Phe Ala Ser Phe Asp Glu Asp Arg Phe<br>155                        160                       165 | 1075 |
| aag aac gag ctg aag aac ggc agg ccc cgg tcc ggc gag acg cgg gcg<br>Lys Asn Glu Leu Lys Asn Gly Arg Pro Arg Ser Gly Glu Thr Arg Ala<br>170                        175                       180 | 1123 |
| gag ttc gag ggc cgc gtc gcg aag gag agc ttc gac gag gag aag ggc<br>Glu Phe Glu Gly Arg Val Ala Lys Glu Ser Phe Asp Glu Glu Lys Gly<br>185                        190                       195 | 1171 |
| ttc cag cgg gcg cgt gag gtg gcg tcc gtc atg aac agg gcc ctg gag<br>Phe Gln Arg Ala Arg Glu Val Ala Ser Val Met Asn Arg Ala Leu Glu<br>200                        205                       210 | 1219 |
| aac gcc cac gac gag agc gct tac ctc gac aac ctc aag aag gaa ctg<br>Asn Ala His Asp Glu Ser Ala Tyr Leu Asp Asn Leu Lys Lys Glu Leu<br>215                        220                       225                       230 | 1267 |
| gcg aac ggc aac gac gcc ctg cgc aac gag gac gcc cgt tcc ccg ttc<br>Ala Asn Gly Asn Asp Ala Leu Arg Asn Glu Asp Ala Arg Ser Pro Phe<br>235                        240                       245 | 1315 |
| tac tcg gcg ctg cgg aac acg ccg tcc ttc aag gag cgg aac gga ggc<br>Tyr Ser Ala Leu Arg Asn Thr Pro Ser Phe Lys Glu Arg Asn Gly Gly<br>250                        255                       260 | 1363 |
| aat cac gac ccg tcc agg atg aag gcc gtc atc tac tcg aag cac ttc<br>Asn His Asp Pro Ser Arg Met Lys Ala Val Ile Tyr Ser Lys His Phe<br>265                        270                       275 | 1411 |
| tgg agc ggc cag gac cgg tcg agt tcg gcc gac aag agg aag tac ggc<br>Trp Ser Gly Gln Asp Arg Ser Ser Ser Ala Asp Lys Arg Lys Tyr Gly<br>280                        285                       290 | 1459 |
| gac ccg gac gcc ttc cgc ccc gcc ccg ggc acc ggc ctg gtc gac atg<br>Asp Pro Asp Ala Phe Arg Pro Ala Pro Gly Thr Gly Leu Val Asp Met<br>295                        300                       305                       310 | 1507 |
| tcg agg gac agg aac att ccg cgc agc ccc acc agc ccc ggt gag gga<br>Ser Arg Asp Arg Asn Ile Pro Arg Ser Pro Thr Ser Pro Gly Glu Gly<br>315                        320                       325 | 1555 |
| ttc gtc aat ttc gac tac ggc tgg ttc ggc gcc cag acg gaa gcg gac<br>Phe Val Asn Phe Asp Tyr Gly Trp Phe Gly Ala Gln Thr Glu Ala Asp<br>330                        335                       340 | 1603 |
| gcc gac aag acc gtc tgg acc cac gga aat cac tat cac gcg ccc aat<br>Ala Asp Lys Thr Val Trp Thr His Gly Asn His Tyr His Ala Pro Asn<br>345                        350                       355 | 1651 |
| ggc agc ctg ggt gcc atg cat gtc tac gag agc aag ttc cgc aac tgg<br>Gly Ser Leu Gly Ala Met His Val Tyr Glu Ser Lys Phe Arg Asn Trp<br>360                        365                       370 | 1699 |
| tcc gag ggt tac tcg gac ttc gac cgc gga gcc tat gtg atc acc ttc<br>Ser Glu Gly Tyr Ser Asp Phe Asp Arg Gly Ala Tyr Val Ile Thr Phe | 1747 |

```
                375                 380                 385                 390
atc ccc aag agc tgg aac acc gcc ccc gac aag gta aag cag ggc tgg          1795
Ile Pro Lys Ser Trp Asn Thr Ala Pro Asp Lys Val Lys Gln Gly Trp
                395                 400                 405 ccg tgatgtgagc g                                                          1809
Pro
```

<210> SEQ ID NO 7
<211> LENGTH: 407
<212> TYPE: PRT
<213> ORGANISM: Streptoverticillium mobaraense

<400> SEQUENCE: 7

```
Met Arg Ile Arg Arg Ala Leu Val Phe Ala Thr Met Ser Ala Val
 1               5                  10                  15

Leu Cys Thr Ala Gly Phe Met Pro Ser Ala Gly Glu Ala Ala Ala Asp
                20                  25                  30

Asn Gly Ala Gly Glu Glu Thr Lys Ser Tyr Ala Glu Thr Tyr Arg Leu
            35                  40                  45

Thr Ala Asp Asp Val Ala Asn Ile Asn Ala Leu Asn Glu Ser Ala Pro
    50                  55                  60

Ala Ala Ser Ser Ala Gly Pro Ser Phe Arg Ala Pro Asp Ser Asp Asp
65                  70                  75                  80

Arg Val Thr Pro Pro Ala Glu Pro Leu Asp Arg Met Pro Asp Pro Tyr
                85                  90                  95

Arg Pro Ser Tyr Gly Arg Ala Glu Thr Val Val Asn Asn Tyr Ile Arg
            100                 105                 110

Lys Trp Gln Gln Val Tyr Ser His Arg Asp Gly Arg Lys Gln Gln Met
        115                 120                 125

Thr Glu Glu Gln Arg Glu Trp Leu Ser Tyr Gly Cys Val Gly Val Thr
    130                 135                 140

Trp Val Asn Ser Gly Gln Tyr Pro Thr Asn Arg Leu Ala Phe Ala Ser
145                 150                 155                 160

Phe Asp Glu Asp Arg Phe Lys Asn Glu Leu Lys Asn Gly Arg Pro Arg
                165                 170                 175

Ser Gly Glu Thr Arg Ala Glu Phe Glu Gly Arg Val Ala Lys Glu Ser
            180                 185                 190

Phe Asp Glu Glu Lys Gly Phe Gln Arg Ala Arg Glu Val Ala Ser Val
        195                 200                 205

Met Asn Arg Ala Leu Glu Asn Ala His Asp Glu Ser Ala Tyr Leu Asp
    210                 215                 220

Asn Leu Lys Lys Glu Leu Ala Asn Gly Asn Asp Ala Leu Arg Asn Glu
225                 230                 235                 240

Asp Ala Arg Ser Pro Phe Tyr Ser Ala Leu Arg Asn Thr Pro Ser Phe
                245                 250                 255

Lys Glu Arg Asn Gly Gly Asn His Asp Pro Ser Arg Met Lys Ala Val
            260                 265                 270

Ile Tyr Ser Lys His Phe Trp Ser Gly Gln Asp Arg Ser Ser Ser Ala
        275                 280                 285

Asp Lys Arg Lys Tyr Gly Asp Pro Asp Ala Phe Arg Pro Ala Pro Gly
    290                 295                 300

Thr Gly Leu Val Asp Met Ser Arg Asp Arg Asn Ile Pro Arg Ser Pro
305                 310                 315                 320

Thr Ser Pro Gly Glu Gly Phe Val Asn Phe Asp Tyr Gly Trp Phe Gly
                325                 330                 335
```

```
Ala Gln Thr Glu Ala Asp Ala Asp Lys Thr Val Trp Thr His Gly Asn
            340                 345                 350

His Tyr His Ala Pro Asn Gly Ser Leu Gly Ala Met His Val Tyr Glu
            355                 360                 365

Ser Lys Phe Arg Asn Trp Ser Glu Gly Tyr Ser Asp Phe Asp Arg Gly
            370                 375                 380

Ala Tyr Val Ile Thr Phe Ile Pro Lys Ser Trp Asn Thr Ala Pro Asp
385                 390                 395                 400

Lys Val Lys Gln Gly Trp Pro
                405

<210> SEQ ID NO 8
<211> LENGTH: 1079
<212> TYPE: PRT
<213> ORGANISM: Streptomyces albogriseolus

<400> SEQUENCE: 8

Asn Gly Glu Asn Ser Thr Ala Ala Gly Ser Ser Ala Ser Ala Thr Ala
 1               5                  10                  15

Leu Lys Gly Lys His Arg Val Thr Leu Ile Thr Gly Asp Arg Val Ala
            20                  25                  30

Leu Asp Ala Lys Gly Arg Val Val Gly Leu Glu Pro Ala Glu Gly Arg
            35                  40                  45

Glu His Ile Pro Val Gln Ile Arg Arg Ser Asp Gly His Thr Leu Val
        50                  55                  60

Val Pro Ala Asp Ala Ala Arg Leu Val Ala Ser Gly Lys Leu Asp Gln
 65                  70                  75                  80

Arg Leu Phe Asp Val Thr Glu Leu Asn Lys Ala Ala Thr Arg Thr Ala
                85                  90                  95

His Arg Gly Gly Leu Lys Val Ile Val Gly Tyr Arg Gly Ala Ala Lys
            100                 105                 110

Ala Ala Lys Ala Asp Val Arg Asp Ala Gly Thr Val Arg Arg Thr Leu
            115                 120                 125

Thr Ser Leu Asn Ala Asp Ala Val Gln Thr Pro Gln Glu Ala Gly Ala
        130                 135                 140

Glu Leu Trp Glu Ala Val Thr Asp Gly Asp Arg Thr Ala Ser Gly Val
145                 150                 155                 160

Ala Arg Val Trp Leu Asp Gly Val Arg Lys Ala Ser Leu Asp Thr Ser
                165                 170                 175

Val Gly Gln Ile Gly Thr Pro Lys Ala Trp Glu Ala Gly Tyr Asp Gly
            180                 185                 190

Lys Gly Val Lys Ile Ala Val Leu Asp Thr Gly Val Asp Ala Thr His
            195                 200                 205

Pro Asp Leu Lys Gly Gln Val Thr Ala Ser Lys Asn Phe Thr Ser Ala
        210                 215                 220

Pro Thr Thr Gly Asp Val Val His Gly Thr His Val Ala Ser Ile
225                 230                 235                 240

Ala Ala Gly Thr Gly Ala Gln Ser Lys Gly Thr Tyr Lys Gly Val Ala
                245                 250                 255

Pro Gly Ala Lys Ile Leu Asn Gly Lys Val Leu Asp Asp Ala Gly Phe
            260                 265                 270

Gly Asp Asp Ser Gly Ile Leu Ala Gly Met Glu Trp Ala Ala Ala Gln
            275                 280                 285

Gly Ala Asp Ile Val Asn Met Ser Leu Gly Gly Met Asp Thr Pro Glu
```

```
                    290                 295                 300
Thr Asp Pro Leu Glu Ala Ala Val Asp Lys Leu Ser Ala Glu Lys Gly
305                 310                 315                 320

Ile Leu Phe Ala Ile Ala Ala Gly Asn Glu Gly Pro Gln Ser Ile Gly
                325                 330                 335

Ser Pro Gly Ser Ala Asp Ser Ala Leu Thr Val Gly Ala Val Asp Asp
            340                 345                 350

Lys Asp Lys Leu Ala Asp Phe Ser Thr Gly Pro Arg Leu Gly Asp
        355                 360                 365

Gly Ala Val Lys Pro Asp Leu Thr Ala Pro Gly Val Asp Ile Thr Ala
370                 375                 380

Ala Ser Ala Lys Gly Asn Asp Ile Ala Lys Glu Val Gly Lys Pro
385                 390                 395                 400

Ala Gly Tyr Met Thr Ile Ser Gly Thr Ser Met Ala Thr Pro His Val
                405                 410                 415

Ala Gly Ala Ala Ala Leu Leu Lys Gln Gln His Pro Glu Trp Lys Tyr
            420                 425                 430

Ala Glu Leu Lys Gly Ala Leu Thr Ala Ser Thr Lys Asp Gly Lys Tyr
        435                 440                 445

Thr Pro Phe Glu Gln Gly Ser Gly Arg Val Gln Val Asp Lys Ala Ile
    450                 455                 460

Thr Gln Thr Val Ile Ala Glu Pro Val Ser Leu Ser Phe Gly Val Gln
465                 470                 475                 480

Gln Trp Pro His Ala Asp Asp Lys Pro Val Thr Lys Lys Leu Thr Tyr
                485                 490                 495

Arg Asn Leu Gly Thr Glu Asp Val Thr Leu Lys Leu Thr Ser Thr Ala
            500                 505                 510

Thr Gly Pro Lys Gly Lys Ala Ala Pro Ala Gly Phe Phe Thr Leu Gly
        515                 520                 525

Ala Ser Thr Leu Thr Val Pro Ala Asn Gly Thr Ala Ser Val Asp Val
    530                 535                 540

Thr Ala Asp Thr Arg Leu Gly Gly Ala Val Asp Gly Thr Tyr Ser Ala
545                 550                 555                 560

Tyr Val Val Ala Thr Gly Ala Gly Gln Ser Val Arg Thr Ala Ala Ala
                565                 570                 575

Val Glu Arg Glu Val Glu Ser Tyr Asn Val Thr Leu Lys Val Leu Asp
            580                 585                 590

Arg Ser Gly Lys Ala Thr Ala Asn Tyr Met Ala Tyr Leu Ser Gly Leu
        595                 600                 605

Thr Gly Leu Gly Lys Asp Arg Ser Tyr Ala Pro Tyr Glu Ala Asp Gly
    610                 615                 620

Ala Val Ser Val Arg Val Pro Lys Gly Gly Tyr Val Leu Asp Ala Ser
625                 630                 635                 640

Val Leu Val Gly Ala Asp Pro Glu Thr Trp Arg Gly Ala Asp Trp Leu
                645                 650                 655

Ala Gln Pro Lys Leu Asp Val Thr Arg Asn Thr Thr Val Thr Val Asp
            660                 665                 670

Ala Arg Lys Ala Lys Pro Val Lys Val Thr Val Pro Gly Lys Ala Ala
        675                 680                 685

Lys Ala Gln Phe Ala Ser Ala Asp Tyr Thr Ile Glu Thr Asn Asp Ser
    690                 695                 700

Ala Val Ser Tyr Gly Trp Trp Leu Glu Asn Tyr Ser Gly Phe Arg Ser
705                 710                 715                 720
```

Ala His Leu Gly Pro Gln Ile Thr Asn Gly Thr Leu Ser Gln Gln Trp
            725                 730                 735

Asn Thr His Phe Ser Asn Gly Ala Lys Ala Gln Tyr Thr Ala Ile Ser
            740                 745                 750

Gly Gly Lys Val Lys Leu Ala Thr Gly Tyr Thr Arg Ala Phe Lys
            755                 760                 765

Ala Lys Glu Phe Ala Thr Val Gln Val Gly Met Gly Ala Ala Ser
770                 775                 780

Gly Lys Lys Gly Ala Val Thr Ala Phe Gly Trp Leu Pro Gly Ser Ser
785                 790                 795                 800

Gly Ala Ser Gly Phe Ser Gln Glu Gln Lys Leu Pro Ser Thr Arg Thr
                805                 810                 815

Leu Tyr Leu Ser Thr Val Asn Gly Val Thr Trp Asp Leu Asp Phe Glu
            820                 825                 830

Gln Leu Gly Gly Val Asp Asn Glu Gly Trp Pro Ile Tyr Asp Ala Val
            835                 840                 845

Tyr Thr Ile Gly Val Gly Lys Thr Tyr Lys Gly Gly Lys Thr Tyr Lys
850                 855                 860

Glu Thr Val Asn Thr Ala Val Phe Gly Pro Arg Leu Thr Ser Ser Tyr
865                 870                 875                 880

Gly Val Phe Arg Asp Gly Asn Ser Ile Tyr Gly Val Ile Pro Leu Phe
                885                 890                 895

Ala Asp Gly Lys Gly His Ala Gly Ser Ser Glu Phe Ser Ser Ala Val
            900                 905                 910

Thr Thr Leu Tyr Arg Asn Gly Lys Lys Val Gly Ser Asn Asn Asp Pro
            915                 920                 925

Leu Phe Gly Glu Glu Gly Phe Thr Val Pro Ser Gly Asp Ala Ala Tyr
            930                 935                 940

Arg Leu Thr Thr Ser Val Lys Arg Ser Ala Lys Val Ala Ala Ala Ser
945                 950                 955                 960

Thr Arg Ile Asp Ala Ser Trp Thr Phe Arg Ser Lys Lys Thr Ser Gly
                965                 970                 975

Glu Lys Gln Leu Pro Val Ser Ser Ala Arg Phe Ala Ala Val Thr Gly
            980                 985                 990

Leu Asp Ser Lys Val Ala Ala Gly Lys Lys Ala Thr Phe Pro Val Val
            995                 1000                1005

Val Glu Gly Ala Ala Gln Gly Lys Asn Leu Lys Ser Leu Ala Val Tyr
1010                1015                1020

Val Ser Tyr Asn Gly Gly Lys Thr Trp Lys Lys Thr Thr Val Thr Lys
1025                1030                1035                1040

Gly Lys Ile Thr Val Lys Asn Pro Ala Lys Gly Lys Ala Ile Ser Phe
                1045                1050                1055

Arg Ala Lys Ile Thr Asp Lys Lys Gly Asn Ala Ser Leu Ile Thr Ile
            1060                1065                1070

His Asn Ala Tyr Tyr Gly Lys
        1075

<210> SEQ ID NO 9
<211> LENGTH: 1751
<212> TYPE: DNA
<213> ORGANISM: Streptoverticillium mobaraense
<220> FEATURE:
<221> NAME/KEY: CDS
<222> LOCATION: (229)..(1659)

-continued

<400> SEQUENCE: 9

```
gctcctatga gcatcgacgc cgccagcagc gatcggttcg gtctgaccgt cgacgccgac      60
ggcgagcgcg tgtggctgga cgagcccggt cggcccgtgc cgctcgtgcg gccgtgaaag     120
gcccgaaaag agcccaagcc gtgtgaactg cgaggacaaa gggtctggcg caacgcatgt     180
caccccagat aagttcgccg cgacctttgc gaacccaggg gagggcgc atg cgc aag      237
                                                    Met Arg Lys
                                                      1
```

| | | | | | | | | | | | | | | | | |
|---|---|---|---|---|---|---|---|---|---|---|---|---|---|---|---|---|
| gct | ctc | aga | tcg | ctg | ctg | gcg | gcg | tcg | atg | ctc | ata | gga | gcg | atc | ggc | 285 |
| Ala | Leu | Arg | Ser | Leu | Leu | Ala | Ala | Ser | Met | Leu | Ile | Gly | Ala | Ile | Gly | |
| | 5 | | | | 10 | | | | | 15 | | | | | | |
| gcc | ggc | agc | gcc | acg | gcg | gag | gcg | gcg | tcg | atc | acc | gcc | ccg | cag | gcc | 333 |
| Ala | Gly | Ser | Ala | Thr | Ala | Glu | Ala | Ala | Ser | Ile | Thr | Ala | Pro | Gln | Ala | |
| 20 | | | | | 25 | | | | | 30 | | | | | 35 | |
| gac | atc | aag | gac | cgc | atc | ctg | aag | att | ccc | ggg | atg | aag | ttc | gtc | gag | 381 |
| Asp | Ile | Lys | Asp | Arg | Ile | Leu | Lys | Ile | Pro | Gly | Met | Lys | Phe | Val | Glu | |
| | | | | 40 | | | | | 45 | | | | | 50 | | |
| gag | aag | ccc | tac | cag | ggc | tac | cgc | tac | ctc | gtg | atg | acg | tac | cgg | cag | 429 |
| Glu | Lys | Pro | Tyr | Gln | Gly | Tyr | Arg | Tyr | Leu | Val | Met | Thr | Tyr | Arg | Gln | |
| | | | 55 | | | | | 60 | | | | | 65 | | | |
| ccg | gtg | gac | cac | cgc | aat | ccc | ggc | aag | ggg | acc | ttc | gag | cag | cgc | ttc | 477 |
| Pro | Val | Asp | His | Arg | Asn | Pro | Gly | Lys | Gly | Thr | Phe | Glu | Gln | Arg | Phe | |
| | 70 | | | | | 75 | | | | | 80 | | | | | |
| acc | ctg | ctc | cac | aag | gac | acc | gac | cgg | ccg | acc | gtg | ttc | ttc | acg | tcc | 525 |
| Thr | Leu | Leu | His | Lys | Asp | Thr | Asp | Arg | Pro | Thr | Val | Phe | Phe | Thr | Ser | |
| 85 | | | | | 90 | | | | | 95 | | | | | | |
| ggc | tac | aac | gtc | tcc | acc | aac | ccc | agc | cgc | agc | gag | ccc | acg | cgc | atc | 573 |
| Gly | Tyr | Asn | Val | Ser | Thr | Asn | Pro | Ser | Arg | Ser | Glu | Pro | Thr | Arg | Ile | |
| 100 | | | | | 105 | | | | | 110 | | | | | 115 | |
| gtg | gac | ggc | aac | cag | gtg | tcg | atg | gag | tac | cgg | ttc | ttc | acg | ccg | tcc | 621 |
| Val | Asp | Gly | Asn | Gln | Val | Ser | Met | Glu | Tyr | Arg | Phe | Phe | Thr | Pro | Ser | |
| | | | | 120 | | | | | 125 | | | | | 130 | | |
| cgg | ccg | cag | ccc | gcc | gac | tgg | tcc | aag | ctg | gac | atc | tgg | cag | gcg | gcg | 669 |
| Arg | Pro | Gln | Pro | Ala | Asp | Trp | Ser | Lys | Leu | Asp | Ile | Trp | Gln | Ala | Ala | |
| | | | 135 | | | | | 140 | | | | | 145 | | | |
| agt | gac | cag | cac | cgc | ctg | tac | cag | gcg | ctg | aag | ccg | gtc | tac | ggg | aag | 717 |
| Ser | Asp | Gln | His | Arg | Leu | Tyr | Gln | Ala | Leu | Lys | Pro | Val | Tyr | Gly | Lys | |
| | | 150 | | | | | 155 | | | | | 160 | | | | |
| aac | tgg | ctg | gcc | acg | ggc | ggc | agc | aag | ggc | ggc | atg | acg | gcc | acc | tac | 765 |
| Asn | Trp | Leu | Ala | Thr | Gly | Gly | Ser | Lys | Gly | Gly | Met | Thr | Ala | Thr | Tyr | |
| | 165 | | | | | 170 | | | | | 175 | | | | | |
| ttc | cgc | cgc | ttc | tac | ccg | aac | gac | atg | aac | ggc | acg | gtc | gcc | tac | gtc | 813 |
| Phe | Arg | Arg | Phe | Tyr | Pro | Asn | Asp | Met | Asn | Gly | Thr | Val | Ala | Tyr | Val | |
| 180 | | | | | 185 | | | | | 190 | | | | | 195 | |
| gcg | ccc | aac | gac | gtg | aac | gac | aag | gaa | gac | tcg | gcg | tac | gac | aag | ttc | 861 |
| Ala | Pro | Asn | Asp | Val | Asn | Asp | Lys | Glu | Asp | Ser | Ala | Tyr | Asp | Lys | Phe | |
| | | | | 200 | | | | | 205 | | | | | 210 | | |
| ttc | cag | aac | gtc | ggc | gac | aag | gcg | tgc | cgc | acg | cag | ctc | aac | tcg | gtg | 909 |
| Phe | Gln | Asn | Val | Gly | Asp | Lys | Ala | Cys | Arg | Thr | Gln | Leu | Asn | Ser | Val | |
| | | | 215 | | | | | 220 | | | | | 225 | | | |
| cag | cgc | gag | gcg | ctc | gtc | cgc | cgc | gac | gag | atc | gtc | gcc | cgc | tac | gag | 957 |
| Gln | Arg | Glu | Ala | Leu | Val | Arg | Arg | Asp | Glu | Ile | Val | Ala | Arg | Tyr | Glu | |
| | | 230 | | | | | 235 | | | | | 240 | | | | |
| aag | tgg | gct | aag | gag | aac | ggc | aag | acg | ttc | aag | gtc | gtc | ggc | agc | gcc | 1005 |
| Lys | Trp | Ala | Lys | Glu | Asn | Gly | Lys | Thr | Phe | Lys | Val | Val | Gly | Ser | Ala | |
| | 245 | | | | | 250 | | | | | 255 | | | | | |
| gac | aag | gcg | tac | gag | aac | gtc | gtc | ctc | gac | ctg | gtc | tgg | tcc | ttc | tgg | 1053 |
| Asp | Lys | Ala | Tyr | Glu | Asn | Val | Val | Leu | Asp | Leu | Val | Trp | Ser | Phe | Trp | |
| 260 | | | | | 265 | | | | | 270 | | | | | 275 | |

-continued

```
cag tac cac ctg cag agc gac tgc gcc tcc gtc ccc gcc acc aag gcg    1101
Gln Tyr His Leu Gln Ser Asp Cys Ala Ser Val Pro Ala Thr Lys Ala
            280                 285                 290 tcc acc gac gag ctg tac aag ttc atc gac gac atc tcg ggc ttc gac    1149
Ser Thr Asp Glu Leu Tyr Lys Phe Ile Asp Asp Ile Ser Gly Phe Asp
        295                 300                 305 ggc tac acc gac cag ggc ctg gag cgc ttc acc ccg tac tac tac cag    1197
Gly Tyr Thr Asp Gln Gly Leu Glu Arg Phe Thr Pro Tyr Tyr Tyr Gln
310                 315                 320 gcg ggc acc cag ctc ggc gcc cct acg gtg aag aac ccg cac ctc aag    1245
Ala Gly Thr Gln Leu Gly Ala Pro Thr Val Lys Asn Pro His Leu Lys
            325                 330                 335 ggc gtg ctg cgg tac ccc ggc atc aac cag ccg cgc tcg tac gtc ccc    1293
Gly Val Leu Arg Tyr Pro Gly Ile Asn Gln Pro Arg Ser Tyr Val Pro
        340                 345                 350                 355 cgc gac atc ccg atg acc ttc cgc ccc ggc gcg atg gcg gac gtc gac    1341
Arg Asp Ile Pro Met Thr Phe Arg Pro Gly Ala Met Ala Asp Val Asp
                360                 365                 370 cgc tgg gtg cgc gag gac agc cgg aac atg ctc ttc gtg tac ggg cag    1389
Arg Trp Val Arg Glu Asp Ser Arg Asn Met Leu Phe Val Tyr Gly Gln
            375                 380                 385 aac gac ccg tgg agc ggt gaa ccg ttc cgc ctg ggc aag ggc gcc gcc    1437
Asn Asp Pro Trp Ser Gly Glu Pro Phe Arg Leu Gly Lys Gly Ala Ala
        390                 395                 400 gcc cgg cac gac tac cgc ttc tac gcc ccg ggc ggc aac cac ggt tcc    1485
Ala Arg His Asp Tyr Arg Phe Tyr Ala Pro Gly Gly Asn His Gly Ser
    405                 410                 415 aac atc gcc cag ttg gtg gcc gac gag cgg gcc aag gcc acg gcc gag    1533
Asn Ile Ala Gln Leu Val Ala Asp Glu Arg Ala Lys Ala Thr Ala Glu
420                 425                 430                 435 gtc ctg aag tgg gcc ggt gtg gcg ccg cag gcc gtc cag aag gac gag    1581
Val Leu Lys Trp Ala Gly Val Ala Pro Gln Ala Val Gln Lys Asp Glu
                440                 445                 450 aag gcc gcc aag ccg ctc gcg ccg ttc gac gcc aag ctc gac cgc gtg    1629
Lys Ala Ala Lys Pro Leu Ala Pro Phe Asp Ala Lys Leu Asp Arg Val
            455                 460                 465 aag aac gac aag cag agc gcg ctg cgt ccg tagggaccca gtgcgtaagg      1679
Lys Asn Asp Lys Gln Ser Ala Leu Arg Pro
        470                 475 cggcgggcgc tcccggcgag gggcgcccgc cgtcgcgttc cggaaggccc cgggtgccgc  1739
cgccggtgct tc                                                     1751
```

<210> SEQ ID NO 10
<211> LENGTH: 477
<212> TYPE: PRT
<213> ORGANISM: Streptoverticillium mobaraense

<400> SEQUENCE: 10

```
Met Arg Lys Ala Leu Arg Ser Leu Leu Ala Ala Ser Met Leu Ile Gly
 1               5                  10                  15

Ala Ile Gly Ala Gly Ser Ala Thr Ala Glu Ala Ala Ser Ile Thr Ala
             20                  25                  30

Pro Gln Ala Asp Ile Lys Asp Arg Ile Leu Lys Ile Pro Gly Met Lys
         35                  40                  45

Phe Val Glu Glu Lys Pro Tyr Gln Gly Tyr Arg Tyr Leu Val Met Thr
     50                  55                  60

Tyr Arg Gln Pro Val Asp His Arg Asn Pro Gly Lys Gly Thr Phe Glu
 65                  70                  75                  80
```

-continued

```
Gln Arg Phe Thr Leu Leu His Lys Asp Thr Asp Arg Pro Thr Val Phe
                 85                  90                  95

Phe Thr Ser Gly Tyr Asn Val Ser Thr Asn Pro Ser Arg Ser Glu Pro
            100                 105                 110

Thr Arg Ile Val Asp Gly Asn Gln Val Ser Met Glu Tyr Arg Phe Phe
        115                 120                 125

Thr Pro Ser Arg Pro Gln Pro Ala Asp Trp Ser Lys Leu Asp Ile Trp
    130                 135                 140

Gln Ala Ala Ser Asp Gln His Arg Leu Tyr Gln Ala Leu Lys Pro Val
145                 150                 155                 160

Tyr Gly Lys Asn Trp Leu Ala Thr Gly Ser Lys Gly Met Thr
                165                 170                 175

Ala Thr Tyr Phe Arg Arg Phe Tyr Pro Asn Asp Met Asn Gly Thr Val
            180                 185                 190

Ala Tyr Val Ala Pro Asn Asp Val Asn Asp Lys Glu Asp Ser Ala Tyr
        195                 200                 205

Asp Lys Phe Phe Gln Asn Val Gly Asp Lys Ala Cys Arg Thr Gln Leu
    210                 215                 220

Asn Ser Val Gln Arg Glu Ala Leu Val Arg Arg Asp Glu Ile Val Ala
225                 230                 235                 240

Arg Tyr Glu Lys Trp Ala Lys Glu Asn Gly Lys Thr Phe Lys Val Val
                245                 250                 255

Gly Ser Ala Asp Lys Ala Tyr Glu Asn Val Val Leu Asp Leu Val Trp
            260                 265                 270

Ser Phe Trp Gln Tyr His Leu Gln Ser Asp Cys Ala Ser Val Pro Ala
        275                 280                 285

Thr Lys Ala Ser Thr Asp Glu Leu Tyr Lys Phe Ile Asp Asp Ile Ser
    290                 295                 300

Gly Phe Asp Gly Tyr Thr Asp Gln Gly Leu Glu Arg Phe Thr Pro Tyr
305                 310                 315                 320

Tyr Tyr Gln Ala Gly Thr Gln Leu Gly Ala Pro Thr Val Lys Asn Pro
                325                 330                 335

His Leu Lys Gly Val Leu Arg Tyr Pro Gly Ile Asn Gln Pro Arg Ser
            340                 345                 350

Tyr Val Pro Arg Asp Ile Pro Met Thr Phe Arg Pro Gly Ala Met Ala
        355                 360                 365

Asp Val Asp Arg Trp Val Arg Glu Asp Ser Arg Asn Met Leu Phe Val
    370                 375                 380

Tyr Gly Gln Asn Asp Pro Trp Ser Gly Glu Pro Phe Arg Leu Gly Lys
385                 390                 395                 400

Gly Ala Ala Ala Arg His Asp Tyr Arg Phe Tyr Ala Pro Gly Gly Asn
                405                 410                 415

His Gly Ser Asn Ile Ala Gln Leu Val Ala Asp Glu Arg Ala Lys Ala
            420                 425                 430

Thr Ala Glu Val Leu Lys Trp Ala Gly Val Ala Pro Gln Ala Val Gln
        435                 440                 445

Lys Asp Glu Lys Ala Ala Lys Pro Leu Ala Pro Phe Asp Ala Lys Leu
    450                 455                 460

Asp Arg Val Lys Asn Asp Lys Gln Ser Ala Leu Arg Pro
465                 470                 475
```

<210> SEQ ID NO 11
<211> LENGTH: 30

```
<212> TYPE: DNA
<213> ORGANISM: Artificial Sequence
<220> FEATURE:
<223> OTHER INFORMATION: Description of Artificial Sequence:PCR primer

<400> SEQUENCE: 11
gactccgacg acagggtcac ccctcccgcc                                      30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:PCR primer

<400> SEQUENCE: 12
cgctcacatc acggccagcc ctgctttacc                                      30

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:PCR primer
                        for the promoter region and signal sequence
                        region of S.mobaraense

<400> SEQUENCE: 13
gtgaccctgt cgtcggagtc                                                 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:PCR primer
                        for the promoter region and signal sequence
                        region of S.mobaraense

<400> SEQUENCE: 14
ggcatcctgt cgagcggctc                                                 20

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:PCR primer

<400> SEQUENCE: 15
aaattcctgt gaattagctg atttag                                          26

<210> SEQ ID NO 16
<211> LENGTH: 44
<212> TYPE: DNA
<213> ORGANISM: Artificial Sequence
<220> FEATURE:
<223> OTHER INFORMATION: Description of Artificial Sequence:PCR primer

<400> SEQUENCE: 16
gagctctccg gcgtatgcgc atagaggcga aggctccttg aata                      44

<210> SEQ ID NO 17
<211> LENGTH: 30
<212> TYPE: DNA
<213> ORGANISM: Artificial Sequence
<220> FEATURE:
```

```
<223> OTHER INFORMATION: Description of Artificial Sequence:PCR primer

<400> SEQUENCE: 17
atgcgcatac gccggagagc tctcgtcttc                                    30

<210> SEQ ID NO 18
<211> LENGTH: 47
<212> TYPE: DNA
<213> ORGANISM: Artificial Sequence
<220> FEATURE:
<223> OTHER INFORMATION: Description of Artificial Sequence:PCR primer

<400> SEQUENCE: 18
ggggtgaccc tgtcgtcgga gtcgttgaag ccgttgttga tgttgaa                  47

<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence:PCR primer

<400> SEQUENCE: 19
cttcgtctct tccccgcgc cattgtcagc gaatgctggg atagcaacgc c              51

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence:PCR primer

<400> SEQUENCE: 20
cttcgtctct tccccgcgc cattgtcctg agcgaatgct gggatagcta c              51

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence:PCR primer

<400> SEQUENCE: 21
cttcgtctct tccccgcgc cattgtcgtt gaagccgttg ttgatgttga a              51

<210> SEQ ID NO 22
<211> LENGTH: 51
<212> TYPE: DNA
<213> ORGANISM: Artificial Sequence
<220> FEATURE:
<223> OTHER INFORMATION: Description of Artificial Sequence:PCR primer

<400> SEQUENCE: 22
cttcgtctct tccccgcgc cattgtcagt caggtcgcgg agggtttcct c              51

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:PCR primer

<400> SEQUENCE: 23
gacaatggcg cggggaaga gacgaagtcc                                     30
```

```
<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 24
gcccagaagc ccaaaattga gattt                                          25

<210> SEQ ID NO 25
<211> LENGTH: 52
<212> TYPE: DNA
<213> ORGANISM: Artificial Sequence
<220> FEATURE:
<223> OTHER INFORMATION: Description of Artificial Sequence:PCR primer

<400> SEQUENCE: 25
cttcgtctct tcccccgcgc cattgtctgc cgttgccaca ggtgcggcca gc            52

<210> SEQ ID NO 26
<211> LENGTH: 52
<212> TYPE: DNA
<213> ORGANISM: Artificial Sequence
<220> FEATURE:
<223> OTHER INFORMATION: Description of Artificial Sequence:PCR primer

<400> SEQUENCE: 26
cgcagccagc gatttcatgc gtttcataga ggcgaaggct ccttgaatag gt            52

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:PCR primer

<400> SEQUENCE: 27
atgaaacgca tgaaatcgct ggctgcggcg                                     30

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 28
ggatccggag cttatcgact gcacg                                          25

<210> SEQ ID NO 29
<211> LENGTH: 52
<212> TYPE: DNA
<213> ORGANISM: Artificial Sequence
<220> FEATURE:
<223> OTHER INFORMATION: Description of Artificial Sequence:PCR primer

<400> SEQUENCE: 29
cgcagccagc gatttcatgc gtttcataat tctgtttcct gtgtgaaatt gt            52

<210> SEQ ID NO 30
<211> LENGTH: 1461
<212> TYPE: DNA
<213> ORGANISM: Streptoverticillium cinnamoneum
<220> FEATURE:
<221> NAME/KEY: CDS
<222> LOCATION: (151)..(1398)
```

<400> SEQUENCE: 30

```
cggcggcagc cctccttgcc gccggcgcag cgacgcagga cggcgcggcc aaggccctga      60
gcggcagctc gtcgcaaacc cctccatcgc gtcgtgctct cacatgccct cgtttcacga     120
ggcttcacca caagggagtt attgatttcc atg cac aaa cgt cgg aga ctt ctc      174
                                 Met His Lys Arg Arg Arg Leu Leu
                                  1               5 gcc ttc gcc act gtg ggt gcg gtc ata tgc acc gca gga ttc aca cct      222
Ala Phe Ala Thr Val Gly Ala Val Ile Cys Thr Ala Gly Phe Thr Pro
         10                  15                  20 tcg gtc agc cag gcc gcc agc agt ggc gat ggg gaa gag aag ggg tcc      270
Ser Val Ser Gln Ala Ala Ser Ser Gly Asp Gly Glu Glu Lys Gly Ser
 25                  30                  35                  40 tac gcc gaa acg cac ggc ctg acg gcg gat gac gtc gag agc atc aac      318
Tyr Ala Glu Thr His Gly Leu Thr Ala Asp Asp Val Glu Ser Ile Asn
                 45                  50                  55 gca ctg aac gaa aga gct ctg act ctg ggc caa cct ggc aag cct ccg      366
Ala Leu Asn Glu Arg Ala Leu Thr Leu Gly Gln Pro Gly Lys Pro Pro
             60                  65                  70 aag gaa tta cct ccg agc gcc agc gcg ccc tcc cgg gcc ccc tcc gat      414
Lys Glu Leu Pro Pro Ser Ala Ser Ala Pro Ser Arg Ala Pro Ser Asp
         75                  80                  85 gac cgg gaa act cct ccc gcc gag ccg ctc gac agg atg cct gag gcg      462
Asp Arg Glu Thr Pro Pro Ala Glu Pro Leu Asp Arg Met Pro Glu Ala
 90                  95                 100 tac cgg gcc tac gga ggc agg gcc act acg gtc gtc aac aac tac ata      510
Tyr Arg Ala Tyr Gly Gly Arg Ala Thr Thr Val Val Asn Asn Tyr Ile
105                 110                 115                 120 cgc aag tgg cag cag gtc tac agt cac cgc gac gga aag aaa cag caa      558
Arg Lys Trp Gln Gln Val Tyr Ser His Arg Asp Gly Lys Lys Gln Gln
                125                 130                 135 atg acc gaa gag cag cga gaa aag ctg tcc tac ggt tgc gtt ggc gtc      606
Met Thr Glu Glu Gln Arg Glu Lys Leu Ser Tyr Gly Cys Val Gly Val
            140                 145                 150 acc tgg gtc aac tcg ggc ccc tac ccg acg aac aga ttg gcg ttc gcg      654
Thr Trp Val Asn Ser Gly Pro Tyr Pro Thr Asn Arg Leu Ala Phe Ala
        155                 160                 165 tcc ttc gac gag aac aag tac aag aac gac ctg aag aac acc agc ccc      702
Ser Phe Asp Glu Asn Lys Tyr Lys Asn Asp Leu Lys Asn Thr Ser Pro
    170                 175                 180 cga ccc gat gaa acg cgg gcg gag ttc gag ggt cgc atc gcc aag ggc      750
Arg Pro Asp Glu Thr Arg Ala Glu Phe Glu Gly Arg Ile Ala Lys Gly
185                 190                 195                 200 agt ttc gac gag ggg aag ggt ttc aag cgg gcg cgt gat gtg gcg tcc      798
Ser Phe Asp Glu Gly Lys Gly Phe Lys Arg Ala Arg Asp Val Ala Ser
                205                 210                 215 gtc atg aac aag gcc ctg gaa aat gcc cac gac gag ggg act tac atc      846
Val Met Asn Lys Ala Leu Glu Asn Ala His Asp Glu Gly Thr Tyr Ile
            220                 225                 230 aac aac ctc aag acg gag ctc acg aac aac aat gac gct ctg ctc cgc      894
Asn Asn Leu Lys Thr Glu Leu Thr Asn Asn Asn Asp Ala Leu Leu Arg
        235                 240                 245 gag gac agc cgc tcg aac ttc tac tcg gcg ctg agg aac aca ccg tcc      942
Glu Asp Ser Arg Ser Asn Phe Tyr Ser Ala Leu Arg Asn Thr Pro Ser
    250                 255                 260 ttc aag gaa agg gac ggc ggc aac tac gac ccg tcc aag atg aag gcg      990
Phe Lys Glu Arg Asp Gly Gly Asn Tyr Asp Pro Ser Lys Met Lys Ala
265                 270                 275                 280
```

```
gtg atc tac tcg aag cac ttc tgg agc ggg cag gac cag cgg ggc tcc      1038
Val Ile Tyr Ser Lys His Phe Trp Ser Gly Gln Asp Gln Arg Gly Ser
            285                 290                 295 tcc gac aag agg aag tac ggc gac ccg gaa gcc ttc cgc ccc gac cag      1086
Ser Asp Lys Arg Lys Tyr Gly Asp Pro Glu Ala Phe Arg Pro Asp Gln
        300                 305                 310 ggt acc ggc ctg gtc gac atg tcg aag gac aga agc att ccg cgc agt      1134
Gly Thr Gly Leu Val Asp Met Ser Lys Asp Arg Ser Ile Pro Arg Ser
    315                 320                 325 ccg gcc aag ccc ggc gaa ggt tgg gtc aat ttc gac tac ggt tgg ttc      1182
Pro Ala Lys Pro Gly Glu Gly Trp Val Asn Phe Asp Tyr Gly Trp Phe
330                 335                 340 ggg gct caa aca gaa gcg gat gcc gac aaa acc aca tgg acc cac ggc      1230
Gly Ala Gln Thr Glu Ala Asp Ala Asp Lys Thr Thr Trp Thr His Gly
345                 350                 355                 360 gac cac tac cac gcg ccc aat agc gac ctg ggc ccc atg cac gta cac      1278
Asp His Tyr His Ala Pro Asn Ser Asp Leu Gly Pro Met His Val His
                365                 370                 375 gag agc aag ttc cgg aag tgg tct gcc ggg tac gcg gac ttc gac cgc      1326
Glu Ser Lys Phe Arg Lys Trp Ser Ala Gly Tyr Ala Asp Phe Asp Arg
            380                 385                 390 gga gcc tac gtg atc acg ttc ata ccc aag agc tgg aac acc gcc ccc      1374
Gly Ala Tyr Val Ile Thr Phe Ile Pro Lys Ser Trp Asn Thr Ala Pro
        395                 400                 405 gcc aag gtg gag caa ggc tgg ccg tgacaggctg gtactacgac ctctgctgat    1428
Ala Lys Val Glu Gln Gly Trp Pro
    410                 415 ttctgcccgg tcagtccacg cctctcgacg cga                                 1461

<210> SEQ ID NO 31
<211> LENGTH: 416
<212> TYPE: PRT
<213> ORGANISM: Streptoverticillium cinnamoneum

<400> SEQUENCE: 31

Met His Lys Arg Arg Leu Leu Ala Phe Ala Thr Val Gly Ala Val
 1               5                  10                  15

Ile Cys Thr Ala Gly Phe Thr Pro Ser Val Ser Gln Ala Ala Ser Ser
                20                  25                  30

Gly Asp Gly Glu Glu Lys Gly Ser Tyr Ala Glu Thr His Gly Leu Thr
            35                  40                  45

Ala Asp Asp Val Glu Ser Ile Asn Ala Leu Asn Glu Arg Ala Leu Thr
        50                  55                  60

Leu Gly Gln Pro Gly Lys Pro Pro Lys Glu Leu Pro Pro Ser Ala Ser
65                  70                  75                  80

Ala Pro Ser Arg Ala Pro Ser Asp Asp Arg Glu Thr Pro Pro Ala Glu
                85                  90                  95

Pro Leu Asp Arg Met Pro Glu Ala Tyr Arg Ala Tyr Gly Gly Arg Ala
            100                 105                 110

Thr Thr Val Val Asn Asn Tyr Ile Arg Lys Trp Gln Gln Val Tyr Ser
        115                 120                 125

His Arg Asp Gly Lys Lys Gln Gln Met Thr Glu Glu Gln Arg Glu Lys
    130                 135                 140

Leu Ser Tyr Gly Cys Val Gly Val Thr Trp Val Asn Ser Gly Pro Tyr
145                 150                 155                 160

Pro Thr Asn Arg Leu Ala Phe Ala Ser Phe Asp Glu Asn Lys Tyr Lys
                165                 170                 175
```

```
Asn Asp Leu Lys Asn Thr Ser Pro Arg Pro Asp Glu Thr Arg Ala Glu
            180                 185                 190

Phe Glu Gly Arg Ile Ala Lys Gly Ser Phe Asp Glu Gly Lys Gly Phe
        195                 200                 205

Lys Arg Ala Arg Asp Val Ala Ser Val Met Asn Lys Ala Leu Glu Asn
    210                 215                 220

Ala His Asp Glu Gly Thr Tyr Ile Asn Asn Leu Lys Thr Glu Leu Thr
225                 230                 235                 240

Asn Asn Asn Asp Ala Leu Leu Arg Glu Asp Ser Arg Ser Asn Phe Tyr
                245                 250                 255

Ser Ala Leu Arg Asn Thr Pro Ser Phe Lys Glu Arg Asp Gly Gly Asn
            260                 265                 270

Tyr Asp Pro Ser Lys Met Lys Ala Val Ile Tyr Ser Lys His Phe Trp
        275                 280                 285

Ser Gly Gln Asp Gln Arg Gly Ser Ser Asp Lys Arg Lys Tyr Gly Asp
    290                 295                 300

Pro Glu Ala Phe Arg Pro Asp Gln Gly Thr Gly Leu Val Asp Met Ser
305                 310                 315                 320

Lys Asp Arg Ser Ile Pro Arg Ser Pro Ala Lys Pro Gly Glu Gly Trp
                325                 330                 335

Val Asn Phe Asp Tyr Gly Trp Phe Gly Ala Gln Thr Glu Ala Asp Ala
            340                 345                 350

Asp Lys Thr Thr Trp Thr His Gly Asp His Tyr His Ala Pro Asn Ser
        355                 360                 365

Asp Leu Gly Pro Met His Val His Glu Ser Lys Phe Arg Lys Trp Ser
    370                 375                 380

Ala Gly Tyr Ala Asp Phe Asp Arg Gly Ala Tyr Val Ile Thr Phe Ile
385                 390                 395                 400

Pro Lys Ser Trp Asn Thr Ala Pro Ala Lys Val Glu Gln Gly Trp Pro
                405                 410                 415
```

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence:PCR primer

<400> SEQUENCE: 32
ggcgatgggg aagagaaggg g         21

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence:PCR primer

<400> SEQUENCE: 33
ggcggatcct cgcgtcgaga ggcgtggact ga         32

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence:PCR primer

<400> SEQUENCE: 34
tacgaattcg agctcggtac c                                              21

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence:PCR primer

<400> SEQUENCE: 35 cccttctct tccccatcgc ctgccgttgc cacaggtgcg gcc                       43

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence:PCR primer

<400> SEQUENCE: 36
aacggggaga acagcacggc cgccgg                                         26

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence:PCR primer

<400> SEQUENCE: 37
ggcgaattct ccggcgggcc gtcaccggt                                      29

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence:PCR primer
                        for fused prepro-serineprotease construction

<400> SEQUENCE: 38
ggcaagctta aattcctgtg aattagctga                                     30

<210> SEQ ID NO 39
<211> LENGTH: 44
<212> TYPE: DNA
<213> ORGANISM: Artificial Sequence
<220> FEATURE:
<223> OTHER INFORMATION: Description of Artificial Sequence:PCR primer
                        for fused prepro-serineprotease gene
                        construction

<400> SEQUENCE: 39
cggccgtgct gttctccccg tttgccgttg ccacaggtgc ggcc                     44

<210> SEQ ID NO 40
<211> LENGTH: 20
<212> TYPE: PRT
<213> ORGANISM: Streptoverticillium mobaraence

<400> SEQUENCE: 40

Gln Ala Asp Ile Lys Asp Arg Ile Leu Lys Ile Pro Gly Met Lys Phe
 1               5                  10                  15
Val Glu Glu Lys
            20

```
<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence:probe for
                        svPEP

<400> SEQUENCE: 41

Lys Ile Pro Gly Met Lys Phe Val Glu Glu Lys
 1               5                  10

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence:probe for
                        svPEP

<400> SEQUENCE: 42
aagatccccg ggatgaagtt cgtcgaggag aag                                    33

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence:PCR primer

<400> SEQUENCE: 43
gaggcggcgt cgatcaccgc ccc                                               23

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence:PCR primer

<400> SEQUENCE: 44
gccaagcttg aagcaccggc ggcggcaccc gg                                     32

<210> SEQ ID NO 45
<211> LENGTH: 46
<212> TYPE: DNA
<213> ORGANISM: Artificial Sequence
<220> FEATURE:
<223> OTHER INFORMATION: Description of Artificial Sequence:PCR primer

<400> SEQUENCE: 45
ggggcggtga tcgacgccgc ctctgccgtt gccacaggtg cggcca                      46

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence:PCR primer

<400> SEQUENCE: 46
gctcggtacc caaattcctg tgaattagct gatttag                                37

<210> SEQ ID NO 47
<211> LENGTH: 24
<212> TYPE: DNA
<213> ORGANISM: Artificial Sequence
```

```
<220> FEATURE:
<223> OTHER INFORMATION: Description of Artificial Sequence:PCR primer

<400> SEQUENCE: 47
gttgaagccg ttgttgatgt tgaa                                              24

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence:PCR primer

<400> SEQUENCE: 48
aacatcaaca acggcttcaa caattccgat tctgagtgcc ct                          42

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 49
cggccacgat gcgtccggcg                                                   20

<210> SEQ ID NO 50
<211> LENGTH: 43
<212> TYPE: DNA
<213> ORGANISM: Artificial Sequence
<220> FEATURE:
<223> OTHER INFORMATION: Description of Artificial Sequence:PCR primer

<400> SEQUENCE: 50
agggcactca gaatcggaat ttgccgttgc cacaggtgcg gcc                         43

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence:PCR primer

<400> SEQUENCE: 51
aattccgatt ctgagtgccc t                                                 21

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:PCR  primer

<400> SEQUENCE: 52
gaattcgagc tcggtaccca                                                   20

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence:PCR primer

<400> SEQUENCE: 53
agcgatttca tgcgtttcat agaggcgaag gctccttgaa                             40
```

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence:PCR primer

<400> SEQUENCE: 54
atgaaacgca tgaaatcgct ggc                                    23

<210> SEQ ID NO 55
<211> LENGTH: 53
<212> TYPE: PRT
<213> ORGANISM: Homo sapiens

<400> SEQUENCE: 55

Asn Ser Asp Ser Glu Cys Pro Leu Ser His Asp Gly Tyr Cys Leu His
 1               5                  10                  15

Asp Gly Val Cys Met Tyr Ile Glu Ala Leu Asp Lys Tyr Ala Cys Asn
             20                  25                  30

Cys Val Val Gly Tyr Ile Gly Glu Arg Cys Gln Tyr Arg Asp Leu Lys
         35                  40                  45

Trp Trp Glu Leu Arg
     50

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 56
actgggaggc tatctccatt                                        20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 57
atcgatctga tcacgttaca                                        20

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence:PCR primer

<400> SEQUENCE: 58
tgtaacgtga tcagatcgat tcactggtcg acaccgttga                  40

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 59
acggaagcta ccttcgaggt                                        20

```
<210> SEQ ID NO 60
<211> LENGTH: 4
<212> TYPE: PRT
<213> ORGANISM: Streptoverticillium mobaraense

<400> SEQUENCE: 60

Phe Arg Ala Pro
 1
```

METHODS FOR SECRETORY PRODUCTION OF PROTEINS

This application is a continuation of application PCT/JP02/02978, filed Mar. 27, 2002.

BACKGROUND OF THE INVENTION

The present invention relates to a method of producing a heterologous protein efficiently by secretory production.

A number of methods for the secretory production of heterologous proteins have been previously reported such as those described in the review on the secretory production of a heterologous protein by a bacterium belonging to the genus Bacillus [Microbial. Rev., 57, 109-137 (1993)], the review on the secretory production of a heterologous protein by methylotrophic yeast *Pichia pastoris* [Biotechnol., 11, 905-910 (1993)] and the report on the industrial production of heterologous proteins by the mould belonging to the genus Aspergillus [Biotechnol., 6, 1419-1422 (1988); Biotechnol., 9, 976-981 (1991)].

The transglutaminase produced by the secretory production according to one embodiment of the present invention is an enzyme which catalyzes acyltransfer reaction of γ-carboxylamide groups in the peptide chain of the protein. When the enzyme is reacted with a protein, the formation of the cross-linkage ε-(γ-Glu)-Lys and the replacement of Gln with Glu by deamidation can occur. Transglutaminase has been used to manufacture gelled food products such as jelly, yogurt, cheese or gelled cosmetics and others, and to improve the quality of meat and the like (Japanese publication of examined application No.1-50382). Moreover, transglutaminase is an enzyme having industrially high usefulness in that it has been used to manufacture materials for thermostable microcapsules, carriers for immobilized enzymes, etc.

Transglutaminases derived from animals and from microorganisms (microbial transglutaminase: referred to as 'MTG' hereinafter) have been previously known. The former is a calcium ion-dependent enzyme that is distributed in animal organs, skin, blood, etc. The examples include guinea pig hepatic transglutaminase (K. Ikura et al. Biochemistry 27, 2898 (1988)), human epidermal keratinocyte transglutaminase (M. A. Phillips et al. Proc. Natl. Acad. Sci. USA 87, 9333 (1990)), human blood coagulation factor XIII (A. Ichinose et al. Biochemistry 25, 6900 (1990)) and others.

For the latter, calcium-independent transglutaminases have been discovered from bacteria belonging to the *Streptoverticillium* genus, which include, for example, *Streptoverticillium griseocarneum* IFO 12776, *Streptoverticillium cinnamoneum* sub sp. *cinnamoneum* (hereinafter, *S. cinnamoneum*) IFO 12852, *Streptoverticillium mobaraense* (hereinafter, *S. mobaraense*) IFO 13819 and others (Publication of unexamined Japanese patent application JP-Kokai No. 64-27471). The peptide mapping and the structural analysis of the genes revealed that the primary structure of the transglutaminase produced by these microorganisms shared no homology with transglutaminases from animals (European Patent Application Publication No. 0 481 504 A1).

Because microorganism-derived transglutaminases (MTG) are produced through the purification from the cultures of microorganisms such as described above, there have been problems in terms of the amount and the efficiency and the like. The production of transglutaminase using a genetically engineered procedure has also been attempted. Transglutaminase proteins and the genes thereof have been reported in, for example, Biosci. Biotechnol. Biochem., 58, 82-87(1994); Biosci. Biotechnol. Biochem., 58, 88-92(1994); Biochimie, 80, 313-319(1998); Eur. J. Biochem., 257, 570-576(1998); WO 96/06931; WO 96/22366, etc., which report the expression and production of transglutaminase in host-vector systems such as *Streptomyces lividans, Aspergillus oryzae* and *Escherichia coli*. In addition to this information, a method has been reported wherein a transglutaminase is produced by secretory production in microorganisms such as *E. coli* and yeast (JP-Kokai No. 5-199883) and a method has been reported wherein active MTG is produced by expressing MTG as an inactive fused protein in an inclusion body within *E. coli* and subsequently solubilizing the inclusion body using protein-denaturing agents, and then, reconstituting it through the removal of the denaturing agents (JP-Kokai No.6-30771). However, the problem has been noted that the expression level is significantly low in the secretory production by microorganisms such as *E. coli* or yeast.

On the other hand, there are examples of previous studies for the efficient secretory production of heterologous proteins using a coryneform bacterium including the secretion of nucleases and lipases [U.S. Pat. No. 4,965,197; J. Bacteriol., 174, 1854-1861(1992)] and the secretion of proteases such as subtilisin [Appl. Environ. Microbiol., 61, 1610-1613 (1995)] by *Corynebacterium glutamicum* (hereinafter, *C. glutamicum*), a study on the secretion of cell surface proteins of a coryneform bacterium [International patent application published in Japan No. 6-502548], the secretion of fibronectin-binding protein using this study [Appl. Environ. Microbiol., 63, 4392-4400 (1997)], a report wherein the secretion of proteins was enhanced using a mutated secretory machinery [JP-Kokai No. 11-169182], etc., but there has been a limited number of reports on limited proteins. In light of the accumulated amount of proteins, Appl. Environ. Microbiol., 61, 1610-1613 (1995) describes that about 2.5 mg/ml of protein was accumulated by expressing the alkaline protease gene from *Dichelobacter nodosus* in *C. glutamicum* using a promoter of subtilisin gene (aprE) from *Bacillus subtilis*, ribosome binding site and the sequence of a signal peptide, but U.S. Pat. No. 4,965,197; JP-Kokai No.6-502548; and JP-Kokai No. 11-169182 do not specifically describe the values of the amount of the proteins secreted and accumulated. Furthermore, in the case of the fibronectin-binding protein [Appl. Environ. Microbiol., 63, 4392-4400 (1997)], only the secretory accumulation of the protein of about 2.5 μg/L is confirmed. Thus, there have been no reports that heterologous proteins could be efficiently accumulated in the medium at a practical level.

Additionally a genetic engineering technology for a coryneform bacterium has been developed in the system using plasmid and phage, such as the establishment of the transformation by protoplast [J. Bacteriol., 159, 306-311 (1984); J. Bacteriol., 161, 463-467(1985)], the development of a various type of vectors [Agric. Biol. Chem., 48, 2901-2903(1984); J. Bacteriol., 159, 306-311(1984); J. Gen. Microbiol., 130, 2237-2246(1984); Gene, 47, 301-306 (1986); Appl. Microbiol. Biotechnol., 31, 65-69(1989)], the development of the regulation method of gene expression [Bio/Technology, 6, 428-430(1988)] and the development of cosmid [Gene, 39, 281-286(1985)]. Moreover there are reports on the cloning of genes from a coryneform bacterium [Nucleic Acids Res., 14, 10113-1011(1986); J. Bacteriol., 167, 695-702(1986); Nucleic Acids Res., 15, 10598(1987); Nucleic Acids Res., 15, 3922(1987); Nucleic Acids Res., 16, 9859(1988); Agric. Biol. Chem., 52, 525-531(1988); Mol.

Microbiol., 2, 63-72(1988); Mol. Gen. Genet., 218, 330-339 (1989); Gene, 77, 237-251(1989)].

Furthermore, a transposable element derived from a coryneform bacterium has also been reported [WO93/18151; EP0445385; JP-Kokai No. 6-46867; Mol. Microbiol., 11, 739-746(1994); Mol. Microbiol., 14, 571-581 (1994); Mol. Gen. Genet., 245, 397-405(1994); FEMS Microbiol. Lett., 126, 1-6(1995); JP-Kokai No. 7-107976].

The transposable element is a DNA fragment that can be transposed on the chromosome and is known to be present in a wide range of organisms ranging from prokaryotes to eukaryotes. Transposons using transposable elements have been developed [WO93/18151; JP-Kokai No. 7-107976; Mol. Gen. Genet., 245, 397-405(1994); JP-Kokai No. 9-70291] and a heterologous gene is able to be expressed using a transposon.

SUMMARY OF THE INVENTION

The object of the invention is to provide a method for the production of a heterologous protein by making a coryneform bacterium to produce an industrially useful heterologous protein, for example, transglutaminase, and efficiently secrete the product extracellularly (i.e., secretory production).

The inventors of the present invention found a mutant which had remarkably higher production capacity in the production of heterologous proteins using coryneform bacteria compared to the wild type *Corynebacterium glutamicum* ATCC13869, which led to the present invention.

Accordingly, the present invention is a method of producing heterologous proteins characterized in that a fusion protein is produced and secreted (secreto-produced) by a mutant coryneform bacterium which has a capacity of secreting the heterologous protein, which is connected to the downstream of the signal peptide from a coryneform bacterium, at least 2-fold higher than the wild type *Corynebacterium glutamicum* ATCC13869.

More specifically, the invention is a method to obtain a large amount of an intended heterologous protein, for example, transglutaminase, by introducing a genetic expression construct into a coryneform bacterium, culturing the thus transformed coryneform bacterium, efficiently secreting the resulting protein extracellularly and recovering the released protein, wherein the genetic expression construct contains a gene sequence encoding an intended protein which is ligated to the downstream of a sequence encoding the signal peptide derived from a coryneform bacterium, especially the signal peptide of a cell surface protein.

As used herein, "the secretion" of a protein or peptide refers to the transportation of the protein or peptide molecule outside the bacterium cell (extracellular transportation) including the case where the protein or peptide molecule exist finally in completely free form in the medium as well as the case where only the part of the protein or peptide molecule is present outside the cell and the case where they are located on the surface of the cell.

DESCRIPTION OF THE PREFERRED EMBODIMENTS

According to the method of the invention, a coryneform bacterium is used as a host vector system, and a large amount of an extracellularly secreted interested protein may be obtained by generating an expression construct wherein the gene encoding the interested protein is ligated to the downstream of the signal peptide of cell surface protein from coryneform bacterium, introducing the construct into a coryneform bacterium and expressing it.

The proteins which may be secreto-produced by the method of the present invention include enzymes, physiologically active proteins and peptides which are industrially useful. Transglutaminase, which is secreto-produced in one embodiment of the present invention, is widely used in the food processing, the manufacture of pharmaceuticals and the like.

A secretory protein has been generally known to be translated as a prepeptide or prepropeptide and thereafter to be formed into a mature protein. That is to say, in general, it has been known that it is translated as a prepeptide or prepropeptide, then the signal peptide ("a pre-part") is cleaved, thereby it is converted into a mature peptide or propeptide by further cleaving of the pro-part with a protease. As used herein, "a signal sequence" refers to the sequence which is located at the N-terminal of a secretory protein precursor and which is not present in a naturally occurring mature protein, and "a signal peptide" refers to the peptide which is cleaved from such a protein precursor. Generally, a signal sequence is cleaved coupling the extracellular secretion by a protease (generally referred to signalpeptidase). Although such a signal peptide shares certain common features in the sequence over species, a signal peptide which has secretory function in one species does not necessarily have the same secretory function in another species.

As used herein, a protein which contains both a signal peptide and a pro-part, that is, a primary translational product can be referred to "a preproprotein," and a protein which does not contain a signal peptide but does contain a pro-part can be referred to "a proprotein." A pro-part of a proprotein can be referred to as "a pro-structure part" or "a pro-structure." "A pro-structure part/pro-structure" of a protein can be herein interchangeably used with "a pro-part" of a protein. The signal peptide in a preproprotein or preprotein may be derived from the different protein or may be a signal peptide naturally occurring in the intended protein and it is preferably derived from a secretory protein of the host to be used. Alternatively, it may be modified to have the optimum codon depending on the codon usage of the host to be used.

Moreover, the signal peptide that can be used for the purpose of the invention may contain a part of the N-terminal amino acid sequence of a naturally occurring mature protein from which the signal peptide is derived. A preproprotein can be especially called "a heterologously fused preproprotein" when the signal peptide is derived from the different protein. For example, when a protein is transglutaminase, they are referred to as "preprotransglutaminase," "protransglutaminase," and "heterologously fused preprotransglutaminase," respectively. A protein in which "the pro-part is cleaved" is referred to a protein wherein at least one or more amino acid that constitute its pro-part is removed by cleaving the peptide bond, including a protein having identical N-terminal amino acid with the naturally occurring protein and also includes a protein having one or more extra amino acids at the N-terminal deriving from the pro-part compared to the naturally occurring protein, and a protein having shorter amino acids sequence than that of a naturally occurring mature protein, provided that the protein has an activity of the intended protein.

As is described in the "Background of the Invention," a limited number of reports have been shown where the extracellular secretory production of a heterologous protein has been achieved using coryneform bacterium and the secretory production method have not been technically established. Also, it has not been known that a coryneform bacterium extracellularly secretes by itself a protein such as a protease. The known examples are endogenous DNase [U.S. Pat. No. 4,965,197] and the fact that the cell surface protein used in the present invention falls off from the cell surface to be found outside the cell [JP-Kokai No. 6-502548]. However, any signal peptide that involves in the secretion of a protein of coryneform bacterium has not been known except for the cell surface proteins. The only known cell surface proteins from coryneform bacterium, to date, are genes for PS1 and PS2, the cell surface proteins of *Corynebacterium glutamicum* [JP-Kokai No. 6-502548], and the gene for SlpA, the cell surface protein of *Corynebacterium ammoniagenes* (which may be abbreviated as *C. ammoniagenes* hereinafter) [JP-Kokai No.10-108675]. Among these proteins, PS1 and SlpA share some homology (about 30%), but almost no homology was found among the others, and furthermore no homology was found in the signal sequence domain any of the proteins. As the examples of signal sequences, the signal sequences of PS1 and PS2 from *Corynebacterium glutamicum* are shown in SEQ ID NO: 1 and SEQ ID NO:2, and the signal sequence of SlpA from *Corynebacterium ammoniagenes* is shown in SEQ ID NO: 3.

Therefore, the inventors cloned the gene of PS2 protein from *C. glutamicum* (formerly, *Brevibacterium lactofermentum*) ATCC13869 strain and determined the sequence. It was found that there were no differences in the signal sequence domain from the known sequence from *C. glutamicum*, but that there were two different amino acids in the sequence up to the N-terminal thirty-eighth amino acid residue of the mature cell surface protein (Asn for Thr residue at position 40 and Glu for Gly residue at position 55 in the amino acid sequence shown in SEQ ID NO: 5). The nucleotide sequence encoding sixty eight residues comprising thirty amino acid residues of the signal peptide and thirty eight amino acid residues from the N-terminal of the mature cell surface protein and its 5'-upstream region containing the promoter region is shown in SEQ ID NO: 4 and the amino acid sequence is shown in SEQ ID NO: 5.

Then, the inventor examined the secretion of a heterologous protein using the region containing the promoter region or the signal peptide region of the cell surface protein in order to determine whether the extracellular secretory production of a large amount of the heterologous protein can be achieved in a coryneform bacterium.

Since the transglutaminase gene from an actinomycete has a high GC content and the gene from a coryneform bacterium has a similar GC content to the gene from actinomycetes and also similar codon usage, there is an advantage that the gene from actinomycetes can be directly used. Therefore, the inventor investigated whether a transglutaminase gene from actinomycetes can be directly used or not, and found that the signal peptide of transglutaminase from actinomycetes did not successfully function in a coryneform bacterium. However, it is revealed that the transglutaminase gene encoding the mature protein containing the pro-structure part from actinomycetes fused with the signal peptide of the cell surface protein from a coryneform bacterium effectively functioned without any modification and was efficiently secreted outside the cell as proprotein containing the pro-structure part. When the gene for transglutaminase with the pro-structure part which additionally comprises thirty amino acid residues from the cell surface protein and thirty eight amino acid residues from the N-terminal domain of the mature cell surface protein, for example, the gene for transglutaminase fused with the N-terminal domain of the mature cell surface protein was used, and the efficiency of the extracellular secretion of transglutaminase was further increased.

As used herein, a coryneform bacterium is an aerobic Gram-positive bacillus, which includes bacteria which were previously classified as *Brevibacterium* but currently unified as *Corynebacterium* (Int. J. Syst. Bacteriol., 41, 255(1981)) including Brevibacterium which is closely related to *Corynebacterium*. The use of *Corynebacterium* is advantageous in that it inherently secretes extremely less proteins outside the cell compared to molds, yeasts or bacteria belonging to Bacillus which have been previously recognized as suitable to effect the secretion of a heterologous protein, and which allow the purification process of the product to be easy and shortened when the secretory production of a heterologous protein is conducted. This is excellent in terms of its medium cost, the culturing procedure, and the yield, since it grows well on a simple culture medium such as those composed of ammonia, inorganic salts and so on.

Examples of *Corynebacterium* which can be used as a host bacterium in the present invention are mutants having the capacity of secreting heterologous proteins at least 2-fold higher than wild type *Corynebacterium glutamicum*. These mutants may be derived from wild type strains including *Brevibacterium saccharolyticum* ATCC 14066, *Brevibacterium immariophilum* ATCC 14068, *Brevibacterium lactofermentum* (*Corynebacterium glutamicum*) ATCC 13869, *Brevibacterium roseum* ATCC 13825, *Brevibacterium flavum* (*Corynebacterium glutamicum*) ATCC14067, *Corynebacterium acetoacidophilum* ATCC13870, *Corynebacterium glutamicum* ATCC 13032, *Corynebacterium lilium* (*Corynebacterium glutamicum*) ATCC 15990, *Brevibacterium ammoniagenes* (*Corynebacterium ammoniagenes*) ATCC6871 or from the mutants thereof. The mutants of the present invention include mutant strains defective in the ability to produce glutamate, mutant strains for amino acids production such as lysine and the like, and mutant strains for producing other substances such as nucleic acids, for example, inosine. The mutants of the present invention may be obtained by selecting the strains having increased capacity of secretory production of proteins after UV-radiation or treating the bacteria with a chemical mutagen such as N-methyl-N'-nitrosoguanidine.

Particularly, *Corinebacterium glutamicum* (*C. glutamicum*) AJ12036 (FERM BP-734-originally deposited on Mar. 26, 1984 at presently, Independent Administrative Agency, National Institute of Advance Industrial Science and Technology, Tsukuba Central 6, 1-1, Higashi 1-Chome Tsukuba-shi, Ibaraki-ken, 305-8566 Japan) has the capacity of secretory production of heterologous proteins at least 2-3 fold higher than the parent strain (wild type strain) under the optimum culture condition as measured as the amount of accumulation, which may be due to the mutation in functional genes responsible for the secretion of proteins. Thus, this strain is suitable as a host. Furthermore, it is particularly preferable to use a strain which is derived from such a mutant and which is modified such that it does not produce cellular surface proteins, because the purification of secreted heterologous proteins becomes easier. Such modifications may be conducted by introducing a mutation into the regions encoding the cellular surface proteins or their expression control regions existing on the genome by mutagenesis or using gene recombination techniques.

The genetic construct which can be used in the present invention generally includes a promoter, a sequence encoding a proper signal peptide and a nucleic acid fraction encoding an intended protein, and a regulatory sequence (an operator or terminator, etc.) necessary to express the gene for the intended protein in a coryneform bacterium, at a proper position such that they can function. The intended protein may have a pro-structure part at the N-terminal. Vectors that may be used for this construct are not particularly limited and include any vector which can function in a coryneform bacterium, and may be those which autonomously multiply, such as plasmids or vectors which are integrated into the chromosome of the bacterium. Plasmids derived from coryneform bacteria are particularly preferable. These include, for example, pHM1519 (Agric. Biol. Chem., 48, 2901-2903(1984)), pAM330 (Agric. Biol. Chem., 48, 2901-2903(1984)), and plasmids obtained by modifying them to possess drug-resistant genes.

Artificial transposons and the like may also be used. When a transposon is used, the intended gene is introduced into the chromosome through homologous recombination or by its own transposing ability.

Promoters which can be used in the invention are not particularly limited. Any promoter which can function in the cell of a coryneform bacterium may be generally used. It may also be a promoter derived from a different species, for example, a promoter derived from *E. coli*, such as tac promoter, etc. Among these promoters, a potent promoter is more preferable, including tac promoter, etc.

Examples of promoters derived from a coryneform bacterium include promoters of the genes of cell surface proteins PS1, PS2 and SlpA, promoters of the genes in biosynthetic systems of different amino acids, for example, glutamate dehydrogenase gene in the glutamic acid biosynthetic system, glutamine synthetase gene in the glutamine synthetic system, aspartokinase gene in the lysine biosynthetic system, homoserine dehydrogenase gene in the threonine biosynthetic system, acetohydroxylate synthase gene in the isoleucine and valine biosynthetic system, 2-isopropylmalate synthase gene, glutamate kinase gene in the proline and arginine synthetic system, phosphoribosyl-ATP pyrophosphorylase gene in the histidine biosynthetic synthesis, deoxyarabinoheptoronic acid phosphate (DAHP) synthase gene in the aromatic amino acid biosynthetic system such as tryptophan, tyrosine and phenylalanine, etc., phosphoribosyl pyrophosphate (PRPP) amidotransferase gene, inosinate dehydrogenase gene and guanylate synthase gene in the nucleic acid biosynthetic system such as inosinate and guanylate.

The signal peptide which is used in the present invention is the signal peptide of a secretory protein from the host, Coryneform bacterium, and preferably it is the signal peptide of a cell surface protein from a Coryneform bacterium. Cell surface proteins include PS1 and PS2 derived from *C. glutamicum* (JP-Kokai No. 6-502548), and SlpA derived from *C. Ammoniagenes* (JP-Kokai No.10-108675). The amino acid sequence of PS1 is shown in SEQ ID NO:2, the amino acid sequence of PS2 in SEQ ID NO:1 and the amino acid sequence of SlpA is shown in SEQ ID NO:3. Additionally, it is reported that DNase from a coryneform bacterium also has a signal peptide, as described in U.S. Pat. No. 4,965,197, which may also be used in the present invention.

A portion of N-terminal amino acid sequence of the secretory protein from which the signal peptide derives may be connected to the signal peptide. The signal sequence is cleaved by a signalpeptidase during the extracellular secretion of the translated product. In addition, the gene encoding the signal peptide can be used either in native form or in modified form containing the optimum codons depending on the codon usage in the host to be used.

When these signal peptides are used, the genes encoding intended proteins are connected to the 3'-terminal of the genes encoding the signal peptides and are located such that they are subject to the regulation of expression by the promoters described above.

The useful proteins which can be secreto-produced according to the present invention essentially include, but are not limited to, all of the secretory proteins derived from animals and plants and microorganisms. For example, proteins such as a protease, an exopeptidase, an aminopeptidase, a carboxypeptidase, a collagenase and a chitinase can be secreto-produced according to the present invention. Proteins which are prepared by the secretory production according to the present invention are preferably naturally occurring secretory proteins, more preferably proteins having additional pro-structure parts. Transglutaminase is particularly preferred as a useful protein prepared by the secretory production according to the present invention. As transglutaminase genes, for example, genes for a transglutaminase of secretion type derived from actinomycetes, for example, *S. mobaraense* IFO 13819, *S. cinnamoneum* IFO 12852, *Streptoverticillium griseocarneum* IFO 12776, *Streptomyces lydicus* [WO960693 1], etc. and molds such as Oomyceted [WO9622366], etc can be used for the purpose of the present invention. The genes encoding these proteins can be modified depending on the type of the host to be used and in order to achieve the desired activity, and may comprise the addition, deletion, replacement of one or more amino acid residues, and optionally may be converted to contain the optimum codon depending on the frequency of codon usage in the host.

When the protein produced by the secretory production according to the present invention is the protein naturally expressed as a prepropeptide, it is preferable to use the gene fragment encoding the proprotein containing the pro-structure part (pro-part), although it is not essential. When the gene encoding a preproprotein is used, the pro-part of the protein obtained as the result of the expression of the gene may be cleaved by any appropriate means, for example, by a protease. For this, aminopeptidases, endopeptidases which can cleave at an appropriate site, or more specific proteases may be used. It is preferable to use the proteases which cleave the protein such that the cleaved protein has an equivalent activity or higher activity than that of the naturally occurring protein. Alternately the gene sequence encoding the intended protein or encoding the pro-structure part of the intended protein can also be modified and designed to express the protein having the recognition site for protease specific to the desired location. General molecular biotechnological procedures including such modification techniques, gene cloning techniques and detection techniques for the produced proteins are well known to those skilled in the art and reference can be made to Sambrook et al., 1989, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); F. M. Ausubel et al.(Eds), Current Protocols in Molecular Biology, John Wiley & Sons, Inc. (1994); PCR Technology: Principles and Application for DNA Amplification, H. Erlich, ed., Stockton Press and etc.

The N-terminal region of the protein which may be finally obtained according to the present invention is not necessarily identical to that of the naturally occurring protein and therefore, one to several amino acids may be further added to or deleted from the naturally occurring protein. When a protease is used, it is preferred that the produced protein is cleaved at about the same position as that of the naturally occurring protein in terms of its activity and it is more preferable that it is identical to the mature peptide of a naturally occurring protein. Therefore the specific proteases which cleave the propeptide at the position such that it generates the same protein as the naturally occurring mature protein are generally most preferable. However, for a particular purpose, the peptides having longer or shorter sequence of amino acid residue by one to several residues at the N-terminal compared to the N-terminal of the naturally occurring protein may possess more appropriate activity. Such proteases include, for example, Dispase (available from Boehringer Manheim Co.) which is commercially available and proteases obtained from the culture medium of microorganisms, such as, for example, the culture medium of actinomycetes. Such proteases may be used in an unpurified state or optionally may be used after being purified to the appropriate purity.

Other examples of suitable proteases for removing the pro-part of protransglutaminases derived from Streptomyces is SAMP45, a serine protease produced by *Streptomyces albogriseolus* (hereinafter it may be abbreviated as *S. albogriseolus*). The gene sequence and encoded full length amino acid sequence (1-13: signal sequence, 32-76: pro-part, 77-407: mature transglutaminase) for *S. mobaraense* transglutaminase is shown in SEQ ID:6 and SEQ ID:7, respectively. In the case of *S. mobaraense* protransglutaminase, since SAMP45 cleaves between Ser$^{72}$ and Phe$^{73}$ in the pro-structure part, the resulting protein has the structure where an additional 4 amino acids (Phe-Arg-Ala-Pro, SEQ ID:60) deriving from the C-terminal of pro-part attached to the N-terminal of the naturally occurring mature transglutaminase. The inventors confirmed that such proteins have the transglutaminase activity. The sequence of SAMP45 gene has already been determined and the amino acid sequence of the protein with the additional pro-structure part (proSAMP45) is shown in SEQ ID NO:8 (J. Bacteriol., 179, 430-438 (1997)), as well.

Additionally, mature transglutaminase identical to the naturally occurring transglutaminase can be obtained by using the proline-specific peptidase produced by *S. mobaraense* (svPEP), which has been found by the inventors, together with SAMP45, which results in the removal of the four amino acids of Phe-Arg-Ala-Pro added at the N-terminal.

This svPEP is an enzyme that cleaves specifically the peptides or the peptide analogues represented by the following formula (I) at the site shown with * in the formula, that is, at the carboxyl terminal side of the third or fourth proline residue from the N-terminal:

Y-Pro-*-Z    (I)

wherein Y represents an oligopeptide consisting of two or three amino acid residues and Z represents an amino acid, peptide, amide or ester.

The nucleotide sequence of svPEP gene and the entire encoded amino acid sequence is shown in SEQ ID:9 and SEQ ID:10, respectively. When svPEP is reacted on the protransglutaminase together with a protease in the form of broth of *S. mobaraense* or *S. mobaraense* cells, the pro-structure part can be cleaved completely, resulting in the mature transglutaminase from which the pro-structure part is completely removed. Alternatively, the mature transglutaminase of which pro-structure part is completely removed can be similarly obtained by culturing a coryneform bacterium where pre-pro svPEP gene together with a protease gene are introduced into a coryneform bacterium which releases a protransglutaminase extracellularly by secretory production. Moreover a mature transglutaminase having the same structure as that of a naturally occurring form can be efficiently produced by introducing similarly both SAMP45 gene and svPEP gene into a coryneform bacterium to which pre-protransglutaminase gene has been introduced, and by allowing the bacterium to secreto-produce protransglutaminase and SAM45 as well as svPEP extracellularly or at the surface of the cells.

The method for introducing the genetic constructs that can be used in the present invention into a coryneform bacterium is not limited to particular methods and the methods generally used include, for example, the protoplast method (Gene, 39, 281-286 (1985)), the electroporation method (Bio/Technology, 7, 1067-1070) (1989)), etc. The resulting transformant can be cultured according to the conventional methods and conditions. For example, the transformant can be cultured with a conventional medium containing carbon sources, nitrogen sources and inorganic sources. Trace amount of organic nutrients such as vitamins and amino acids can be optionally added to the medium in order to achieve the growth to greater extent.

Carbohydrates such as glucose and sucrose can be used as carbon sources, and organic acids such as acetic acid, alcohols and others can be used. Gaseous ammonia, aqueous ammonia, ammonium salt and others can be used as nitrogen sources. As inorganic ions, calcium ion, magnesium ion, phosphorus ion, potassium ion, ferrous or ferric ion and others are optionally used as necessary. The culture may be conducted for about 1 to 7 days under the aerobic condition in the appropriate range of pH between 5.0 and 8.5 and of the temperature between 15° C. and 37° C. By culturing the transformant under such conditions, a large amount of an intended protein is produced intracellularly and is efficiently secreted extracellularly. Transglutaminase is generally known to be lethal when it is largely accumulated in the cells of microorganisms, but according to the present invention, transglutaminase is continuously produced without generating lethal effects, because the intracellularly produced transglutaminase is released extracellularly.

The proteins which have been secreted in the medium according to the present invention can be isolated and purified from incubated culture medium according to methods well known to those skilled in the art. For example, the proteins can be isolated and purified by removing the cells from the medium by centrifugation, etc., and then by using known appropriate methods such as salting-out, ethanol precipitation, ultrafiltration, gel filtration chromatography, ion-exchange column chromatography, affinity chromatography, medium high-pressure liquid chromatography, reversed-phase chromatography, hydrophobic chromatography or the combination thereof. The proteins secreted at the surface of the cells according to the present invention can be isolated and purified by using methods well known to those skilled in the art, for example, by solubilizing them with increased salt concentrations or surfactants, and then using similar methods as those used for proteins secreted in the medium. Additionally, in some cases, the proteins secreted at the surface of the cell may be used without solubilization, for example, as immobilized enzymes.

EXAMPLES

The present invention will be illustrated by the following examples, but these examples should not be construed as limiting as to the scope of the present invention.

Example 1

Expression of Prepro-transglutaminase Derived from *S. mobaraense* IFO13819 in *C. glutamicum* ATCC13869

(1) Acquisition of the Transglutaminase Gene Derived from *S. mobaraense* IFO13819

The sequence of transglutaminase gene derived from *S. mobaraense* DSMZ strain has already been determined [Eur. J. Biochem., 257, 570-576(1998)]. The primers shown in SEQ ID NO: 11 and SEQ ID NO: 12 were synthesized with reference to the sequence and the region encoding the sequence of mature transglutaminase was amplified using PCR method with the chromosomal DNA of *S. mobaraense* IFO13819 prepared according to the conventional procedure (the method of Saito and Miura [Biochim, Biophys. Acta, 72, 619(1963)]. For PCR reaction, Pyrobest DNA polymerase (Takarashuzo Co. Ltd.) was used and the reaction condition followed the protocol recommended by the manufacturer.

(SEQ ID NO: 11) 5'-GACTCCGACGACAGGGTCACCCCTCCCGCC-3'

(SEQ ID NO: 12) 5'-CGCTCACATCACGGCCAGCCCTGCTTTACC-3'

SEQ ID NO: 11 and SEQ ID NO: 12: PCR primer

The DNA probe was then generated by conducting the reaction using amplified DNA fragment of about 1.0 kb with [α-$^{32}$P]dCTP and Random Primer DNA Labeling Kit Ver. 2 (Takarashuzo Co. Ltd.) according the protocol attached to the Kit. It was confirmed that the transglutaminase gene was present in the fragment of about 4 kb excised with restriction enzyme Sac I by Southern blot hybridization using the generated probe and the chromosomal DNA of *S. mobaraense* IFO13819 according to the conventional method, as described in Molecular Cloning 2nd edition J. Sambrook, E. F. Fritsch and T. Maniatis, Cold Spring Harbor Laboratory Press, p9. 31 (1989). Accordingly, the fragment of about 4 kb which had been generated by SacI digestion of the chromosomal DNA of *S. mobaraense* IFO13819 was recovered through agarose gel electrophoresis using EASYTRAP Ver. 2 (Takarashuzo Co. Ltd.) and was inserted into Sac I site of pUC18 (Takarashuzo Co. Ltd.) which was introduced into competent cells of *Escherichia coli* JM109 (Takarashuzo Co. Ltd.) to generate a library.

The bacterium strain harboring the plasmid where the transglutaminase gene fragment was cloned was obtained by screening the library using the previously generated DNA probe for transglutaminase by colony hybridization as described in Molecular Cloning 2nd edition J. Sambrook, E. F. Fritsch and T. Maniatis, Cold Spring Harbor Laboratory Press, p1. 90(1989). The plasmid was recovered from this strain and designated as pUITG. The sequence of the fragment cloned in pUITG was determined, which confirmed that the transglutaminase gene from *S. mobaraense* IFO13819 had the same nucleotide sequence as that of the transglutaminase from *S. mobaraense* DSMZ strain.

The determination of the nucleotide sequence revealed that the SacI fragment of about 4 kb was the incomplete DNA fragment from which the signal sequence (the pre-part) was partially deleted. Accordingly, the cloning of the promoter region and the entire signal sequence region was attempted. The cloning was performed using TAKARA LA PCR in vitro Cloning kit (Takarashuzo Co. Ltd.) and the synthesized primers shown in SEQ ID NO: 13 and SEQ ID NO:14 according to the attached protocol.

(SEQ ID NO: 13) 5'-GTGACCCTGTCGTCGGAGTC-3'

(SEQ ID NO: 14) 5'-GGCATCCTGTCGAGCGGCTC-3'

SEQ ID NO: 13 and SEQ ID NO: 14: PCR primers for the promoter region and the signal sequence of *S. mobaraense*

Consequently when a cassette primer of SalI was used, the PCR-amplified fragment of about 800 bp was obtained and the sequencing of the fragment confirmed that the fragment contained the promoter region of the transglutaminase gene and the signal sequence region. Accordingly, the PCR-amplified fragment of about 800 bp was inserted into SmaI site of pVC7 described in JP-Kokai No. 9-070291 to obtain pVITGS5. Additionally plasmid pUITG was digested with SacI, the fragment of about 4 kb was recovered through agarose electrophoresis, and the fragment was inserted to SacI site of pVITGS5 to construct plasmid pVITGC which contained the full-length transglutaminase gene. The determination of the nucleotide sequence was performed using Dye Terminator Cycle Sequencing kit (PE Applied Biosystems) and DNA Sequencer 373A (PE Applied Biosystems). The sequence of the preprotransglutaminase gene is shown in SEQ ID NO: 6. It was supposed that the N-terminal 31 amino acids sequence (No. 1-31) was the signal sequence (the pre-part), the N-terminal 45 amino acids sequence (No.32-76) was the pro-part and the N-terminal 331 amino acids sequence (No.77-407) was the mature transglutaminase.

(2) Conversion of the Promoter Region of Transglutaminase Gene

The sequence of the gene for PS2 which is a surface protein of *C. glutamicum* has already been determined [Mol. Microbiol., 9, 97-109(1993)]. Primers shown as SEQ ID NO: 15 and SEQ ID NO: 16 were synthesized on referring to that sequence, and the region which contains the promoter located at the 5'-upstream region of the initiation codon of PS2 protein gene was amplified using PCR method from the chromosomal DNA of *C. glutamicum* ATCC13869 prepared according to a conventional method.

(SEQ ID NO: 15)

5'-AAATTCCTGTGAATTAGCTGATTTAG-3'

(SEQ ID NO: 16)

5'-GAGCTCTCCGGCGTATGCGCATAGAGGC-GAAGGCTCCTTGAATA-3'

SEQ ID NO: 15 and SEQ ID NO: 16: PCR primers

On the other hand, the primers shown in SEQ ID NO: 12 and SEQ ID NO: 17 were synthesized based on the sequence of the transglutaminase gene determined in Example 1(1), and the region of the preprotransglutaminase gene was amplified using PCR method from pUITG obtained in Example 1(1).

(SEQ ID NO: 12)  5'-CGCTCACATCACGGCCAGCCCTGCTTTACC-3'

(SEQ ID NO: 17)  5'-ATGCGCATACGCCGGAGAGCTCTCGTCTTC-3'

SEQ ID NOs: 12 and 17: PCR primer

Then, the fusion gene of transglutaminase fused with the additional pre-pro structure part, which was ligated to the region comprising the promoter of the cell surface protein gene from C. glutamicum ATCC13869, was amplified by performing cross-over PCR with SEQ ID NO: 15 and SEQ ID NO:12 using the mixture of 1 µl each of the PCR solution of the amplified region comprising the promoter of PS2 gene of C. glutamicum ATCC13869 and of the amplified pre-protransglutaminase gene region, as the templates. The amplified fragment of about 1.8 kb was detected by agarose gel electrophoresis. This fragment was recovered from the agarose gel with EASYTRAP Ver. 2 (Takarashuzo Co. Ltd.) and inserted into SmaI site of pVC7 as described in JP-Kokai No. 9-070291 to obtain pVKPTGO. The nucleotide sequence of the inserted fragment was determined according to the method described above and it was confirmed that the fusion gene was constructed as expected.

(3) Expression of the Pre-Protransglutaminase Gene in C. glutamicum ATCC13869

C. glutamicum ATCC13869 was transformed with the pVITGC constructed in Example 1(1) (both the promoter and the pre-protransglutaminase gene were derived from S. mobaraense) or with the pVKPTGO constructed in Example 1(2) (the promoter was derived from PS2 gene of C. glutamicum ATCC 13869 and the pre-protransglutaminase gene was derived from S. mobaraense) and the strains grown on the CM2S agar medium comprising 5 mg/l of chloramphenicol (10 g of yeast extract, 10 g of tryptone, 5 g of sucrose, 5 g of NaCl, 5 g of agar per liter of distilled water) were selected. The selected C. glutamicum ATCC13869 cells harboring pVITGC or pVKPTGO were cultured in MM culture medium (30 g of glucose, 0.4 g of magnesium sulfate heptahydrate, 30 g of ammonium sulfate, 1 g of potassium dihydrogenphosphate, 0.01 g of ferrous sulfate heptahydrate, 0.01 g of manganese(II) sulfate pentahydrate, 200 µg of thiamine hydrochloride, 500 µg of biotin, 0.15 g of DL-methionine, 50 g of calcium carbonate per liter of distilled water, adjusted to pH 7.5) comprising 5 mg/l of chloramphenicol at 30° C. for 48 hours, respectively. After the incubation was finished, 10 µl of the supernatant of the culture was subjected to SDS-PAGE and then to Western blot using anti-transglutaminase antibody as described in Biosci. Biotechnol. Biochem., 58, 82-87(1994) according to the conventional method (for example, the general procedure as described in J. Sambrook et al. (1989)(supra)).

Consequently, the secretion of transglutaminase could not be detected. From the above results, it was confirmed that the signal sequence of transglutaminase from S. mobaraense did not function in C. glutamicum ATCC13869.

Example 2

Secretory Production of Mature Transglutaminase Using the Fusion Gene Encoding the Signal Peptide of the Cell Surface Protein of Corynebacterium glutamicum (C. glutamicum ATCC 13869) and the Mature Transglutaminase Derived from S. mobaraense IFO13819

(1) Construction of the Transglutaminase Gene Containing the Signal Sequence of Cell Surface Protein of C. glutamicum ATCC13869

The sequence of the gene of PS2 which is the cell surface protein of C. glutamicum has been already determined [Mol. Microbiol., 9, 97-109(1993)]. The primers shown as SEQ ID NO: 15 and SEQ ID NO: 18 were synthesized on referring to the sequence, and the region encoding the N-terminal 44 amino acid residues (30 amino acid residues of the signal peptide and 14 amino acid residues of the mature cell surface protein) of the protein corresponding to PS2 and 5'-upstream region containing the promoter region were amplified using PCR method with the chromosomal DNA of C. glutamicum ATCC13869 prepared according to the method described in Example 1(2). The primer shown in SEQ ID NO:18 also comprises the sequence encoding the amino acid sequence from the N-terminal region of the mature transglutaminase in order to construct the fusion gene fused with transglutaminase.

(SEQ ID NO: 15)

5'-AAATTCCTGTGAATTAGCTGATTTAG-3'

(SEQ ID NO: 18)  5'-GGGGTGACCCTGTCGTCGGAGTCGTTGAAGCCGTTGTTGATGTTGAA-3'

SEQ ID NOs:15 and 18: PCR primer

On the other hand, primers shown in SEQ ID NO:11 and SEQ ID NO: 12 were synthesized based on the sequence of the transglutaminase gene determined in Example 1(1) and the region of mature transglutaminase gene was amplified using PCR method with pUITG obtained in Example 1(1).

The fusion gene of the mature transglutaminase, which was connected to the region encoding the N-terminal 44 amino acid residues of C. glutamicum ATCC13869 and to the 5'-upstream region comprising the promoter gene of the cell surface protein gene, was amplified by performing cross-over PCR with SEQ ID NO:15 and SEQ ID NO:12 using the mixture of 1 µl of PCR solution of the amplified region encoding the N-terminal 44 amino acid residues of the protein corresponding to PS2 of C. glutamicum and of the amplified 5'-upstream region containing the promoter, and 1 µl of PCR solution of the amplified mature transglutaminase gene region, as the templates.

The amplified fragment of about 1.7 kb was detected by agarose electrophoresis. This fragment was recovered from the agarose gel using EASYTRAP Ver. 2 (Takarashuzo Co. Ltd.) and inserted into SmaI site of the pVC7 described in JP-Kokai No. 9-070291 to obtain pVKPTG3. The nucleotide sequence of the inserted fragment was determined according to the method described above and it was confirmed that the expected fusion gene was constructed.

Additionally, the fusion mature transglutaminase gene of about 1.7 kb, which had been ligated to the region encoding the N-terminal 44 amino acid residues from *C. glutamicum* ATCC13869 and the 5'-upstream region comprising the promoter of the cell surface protein gene, was excised by digesting pVKTG3 with KpnI and XbaI and recovered using agarose electrophoresis. This fragment was inserted into the KpnI-XbaI site of pPK4 described in JP-Kokai No. 9-322774 to construct pPKTG3.

(2) Secretion of Mature Transglutaminase Using the Signal Sequence of the Cell Surface Protein of *C. glutamicum* ATCC13869

*C. glutamicum* ATCC13869 was transformed with the constructed plasmid pVKTG3 or pPKTG3 (in both cases the gene comprising the promoter and the gene encoding signal peptide and the N-terminal 14 amino acid residues were derived from *C. glutamicum* ATCC13869, and the mature transglutaminase gene was derived from *S. mobaraense*) and the strains grown on the CM2S agar medium comprising 5 mg/l of chloramphenicol or 25 mg/l of kanamycin and were selected. The selected *C. glutamicum* ATCC13869 cells containing pVITG3 or pVKPTG3 were then cultured in liquid MM culture medium, described above, comprising 5 mg/l of chloramphenicol or 25 mg/l of kanamycin at 30° C. for 48 hours, respectively. After the incubation was finished, 10 μl of the supernatant of the culture was subjected to SDS-PAGE and then Western blot was performed according to a conventional method using anti-transglutaminase antibody as described in Biosci. Biotechnol. Biochem., 58, 82-87(1994). As a result, a small amount of secreted transglutaminase having the similar molecular weight to that of the mature transglutaminase could be detected in the supernatant of the culture of both strains.

Example 3

Secretory Production of Pro-transglutaminase Using Pro-transglutaminase Fusion Gene (Heterologously Fused Prepro-Transglutaminase Fusion Gene) Derived from *S. mobaraense* IFO13819 Ligated to the Signal Peptide of Cell Surface Protein of *C. glutamicum* ATCC13869

(1) Construction of Transglutaminase Gene (Heterologously Fused Preprotransglutaminase Fusion Gene) Containing the Additional Pro-structure Part with the Signal Peptide of Cell Surface Protein of *C. glutamicum* ATCC13869.

The primers shown in SEQ ID NO: 19, SEQ ID NO:20, SEQ ID NO:21 and SEQ ID NO:22 were synthesized on referring to the sequence of the gene of PS2 which was the cell surface protein of *C. glutamicum* [Mol. Microbiol., 9, 97-109(993)]. The coding region for the N-terminal 30, 31, 44 or 68 amino acid residues (the region comprising 30 amino acid residues of the signal peptide) and the 5'-upstream region containing the promoter region of the protein corresponding to PS2 were amplified respectively by PCR method using the combination of SEQ ID NO: 15 and SEQ ID NO: 19, or of SEQ ID NO: 15 and SEQ ID NO:20, or of SEQ ID NO: 15 and SEQ ID NO: 21, or of SEQ ID NO: 15 and SEQ ID NO:22 from the chromosomal DNA of *C. glutamicum* ATCC 13869 prepared according to the method described in Example 1(2).

Primers shown in SEQ ID NO:19, SEQ ID NO:20, SEQ ID NO:21 and SEQ ID NO: 22 comprise the sequences encoding the N-terminal amino acids of pro-transglutaminase in order to construct the fusion gene fused with the transglutaminase having the pro-structure part.

(SEQ ID NO: 15)   5'-AAATTCCTGTGAATTAGCTGATTTAG-3'

(SEQ ID NO: 19)   5'-TTCGTCTCTTCCCCCGCGCCATTGTCAGCGAATGCTGGGATAGCAACGCC-3'

(SEQ ID NO: 20)   5'-CTTCGTCTCTTCCCCCGCGCCATTGTCCTGAGCGAATGCTGGGATAGCTAC-3'

(SEQ ID NO: 21)   5'-CTTCGTCTCTTCCCCCGCGCCATTGTCGTTGAAGCCGTTGTTGATGTTGAA-3'

(SEQ ID NO: 22)   5'-CTTCGTCTCTTCCCCCGCGCCATTGTCAGTCAGGTCGCGGAGGGTTTCCTC-3'

SEQ ID NOs:15, 19, 20, 21 and 22: PCR primers

On the other hand, the primers shown in SEQ ID NO:23 and SEQ ID NO:12 were synthesized based on the sequence of the transglutaminase gene determined in Example 1(1) and the pro-transglutaminase gene region was amplified using PCR method with pUITG obtained in Example 1(1).

(SEQ ID NO: 12)   5'-CGCTCACATCACGGCCAGCCCTGCTTTACC-3'

(SEQ ID NO: 23)   5'-GACAATGGCGCGGGGGAAGAGACGAAGTCC-3'

SEQ ID NOs: 12 and 23: PCR primer

Then the heterologously fused pro-transglutaminase gene ligated to the respective region encoding its N-terminal 30, 31, 44 or 68 amino acid residues and the 5'-upstream region comprising the promoter region of the protein gene corresponding to PS2 from *C. glutamicum* ATCC13869, that is, the fragments of heterologously fused prepro-transglutaminase genes which were ligated to the promoter of the gene of the cell surface protein of *C. glutamicum* ATCC13869, was amplified by performing cross-over PCR with SEQ ID NO: 15 and SEQ ID NO:12 using the mixture which comprises 1 μl of PCR solution of the 5'-upstream region containing the promoter region of the gene of the protein corresponding to PS2 of *C. glutamicum* ATCC13869 and one of the amplified region encoding N-terminal 30, 31, 44 or 68 amino acid residues of the protein, and 1 μl of PCR solution of the amplified region of the gene for the transglutaminase having the pro-structure part, as the templates.

The amplified fragments ranging about 1.8 kb to 1.9 kb was detected by agarose electrophoresis. These fragments were recovered from the agarose gels with EASYTRAP Ver. 2 (Takarashuzo Co. Ltd.) and inserted into SmaI site of pVC7 as described in JP-Kokai No. 9-070291 to obtain pVKPTG1, pVKPTG2, pVKPTG3 and pVKPTG4, respectively. The nucleotide sequences of the inserted fragments were determined according to the aforementioned method and it was confirmed that the expected fusion genes were expected.

Additionally, the fusion genes of about 1.8 kb to 1.9 kb of transglutaminase having the pro-structure parts, which was ligated to the respective region encoding the 30, 31, 44 or 68 amino acid residues and the 5'-upstream region comprising the promoter region of the gene of the protein corresponding to PS2 of *C. glutamicum*, were excised by digesting pVKPTG1, pVKPTG2, pVKPTG3 or pVKPTG4 respectively with KpnI and XbaI and were recovered by agarose electrophoresis. These fragments were inserted into KpnI-XbaI site of pPK4 described in JP-Kokai No. 9-322774 to construct pPKPTG1, pPKPTG2, pPKPTG3 and pPKPTG4.

(2) Secretion of Pro-Transglutaminase Using the Signal Sequence of the Cell Surface Protein of *C. glutamicum* ATCC13869

*C. glutamicum* ATCC 13869 was transformed with the constructed plasmid pVKPTG1, pVKPTG2, pVKPTG3, pVKPTG4, pPKPTG1, pPKPTG2, pPKPTG3 or pPKPTG4 and the strains grown on the CM2S agar medium, described above, comprising 5 mg/l of chloramphenicol or 25 mg/l of kanamycin and selected. The selected *C. glutamicum* ATCC13869 harboring pVKPTG1, pVKPTG2, pVKPTG3, pVKPTG4, pPKPTG1, pPKPTG2, pPKPTG3 or pPKPTG4 were then cultured in MM culture medium, described above, comprising 5 mg/l of chloramphenicol or 25 mg/l of kanamycin at 30° C. for 48 hours, respectively. After the incubation was finished, 10 μl of the supernatant of the culture was subjected to SDS-PAGE and then Western blot was performed using anti-transglutaminase antibody as described in Biosci. Biotechnol. Biochem., 58, 82-87(1994) according to the conventional method. As a result, the secretion of the similar amount of transglutaminase having the pro-structure part was confirmed for both of the vectors, pVC7 or pPK4, and the significant differences in the secreted amount were observed depending on the length of N-terminal amino acid residues of the mature form of the protein corresponding to PS2. The representative secreted amounts are shown in Table 1.

TABLE 1

The secreted amount of pro-transglutaminase using the signal sequence of the cell surface protein of *C. glutamicum* ATCC13869

| plasmid | pro-transglutaminase (mg/l) |
| --- | --- |
| pPKPTG1 | 78 |
| pPKPTG4 | 210 |

Example 4

Secretory Production of Pro-transglutaminase Using the Fusion Gene having the Sequence Encoding the Signal Sequence of the Cell Surface Protein of *C. ammoniagenes* and the Pro-transglutaminase Derived from *S. mobaraense* IFO13819

(1) Construction of the Transglutaminase Gene having the Additional Pro-structure Part and the Signal Sequence of the Cell Surface Protein of *C. ammoniagenes* (Heterologously Fused Preprotransglutaminase Fusion Gene)

The primers shown in SEQ ID NO:24 and SEQ ID NO:25 were synthesized on referring to the sequence of the gene of the cell surface protein (SipA) [JP-Kokai No. 10-108675] of *C. ammoniagenes* and the region comprising the 5'-upstream region containing the promoter region of the cell surface protein (SlpA) gene and the region encoding the N-terminal 25 amino acid residues (the signal peptide) of SlpA was amplified using PCR method from the chromosomal DNA of *C. ammoniagenes* prepared according to the conventional method. The primer shown in SEQ ID NO:25 also comprises the sequence encoding the N-terminal amino acids of the pro-transglutaminase in order to construct the fusion gene fused with the pro-transglutaminase.

(SEQ ID NO: 24) 5'-GCCCAGAAGCCCAAAATTGAGATTT-3'

(SEQ ID NO: 25) 5'-CTTCGTCTCTTCCCCCGCGCCATTGTCTGCCGTTGCCACAGGTGCGGCCAGC-3'

SEQ ID NOs: 24 and 25: PCR primers

The fusion transglutaminase gene containing the additional pro-structure part which was ligated to the region encoding the N-terminal 25 amino acid residues of *C. ammoniagenes* and the 5'-upstream region comprising the promoter region of the cell surface protein (SlpA) gene (heterologously fused prepro-transglutaminase gene) was amplified by performing cross-over PCR with SEQ ID NO:24 and SEQ ID NO: 12 using the mixture, as the templates, containing 1 μl of PCR solution of the amplified 5'-upstream region containing the promoter region of the gene of the cell surface protein (SlpA) and the region encoding the N-terminal 25 amino acid residues of the cell surface protein (SlpA) of *C. ammoniagenes* and 1 µl of PCR solution of the region of the gene for the transglutaminase having the additional pro-structure part which had been amplified in Example 3(1). The amplified fragment of about 1.7 kb was detected by agarose electrophoresis. This fragment was recovered from agarose gel using EASYTRAP Ver. 2 (Takarashuzo Co. Ltd.) and was inserted into SmaI site of pVC7 to obtain pVSPTG1.

(2) Conversion of the Promoter Region: Ligation with the Promoter of the Cell Surface Protein Gene of *C. glutamicum* ATCC 13869

The primers shown in SEQ ID NO: 15 and SEQ ID NO:26 were synthesized on referring to the sequence of the gene of PS2 which is the cell surface protein [Mol. Microbiol., 9, 97-109(1993)] of *C. glutamicum*. The 5'-upstream region comprising the promoter region of the gene for the protein corresponding to PS2 was amplified using PCR method from the chromosomal DNA of *C. glutamicum* ATCC13869 prepared according to the method in Example 1(2). The primer shown in SEQ ID NO:26 also comprises the sequence encoding the N-terminal amino acids of the signal sequence of the cell surface protein (SlpA) of *C. ammoniagenes* in order to construct the fusion gene with transglutaminase gene having the pro-structure part connected to the signal sequence of the cell surface protein (SlpA) of *C. ammoniagenes* (heterologously fused prepro-transglutaminase fusion gene).

µl of PCR solution of the amplified 5'-upstream region containing the promoter region of the gene for the protein corresponding to PS2 of *C. glutamicum* and 1 µl of PCR solution of the amplified region of the gene for the transglutaminase having the pro-structure part which had the signal sequence of the cell surface protein (SlpA) of *C. ammoniagenes* (heterologously fused prepro-transglutaminase gene).

The amplified fragment of about 1.8 kb was detected by agarose electrophoresis. This fragment was recovered from the agarose gel using EASYTRAP Ver. 2 (Takarashuzo Co. Ltd.) and inserted into SmaI site of pVC7 described in JP-Kokai No. 9-070291 to obtain pVKSPTG1. The nucleotide sequence of the inserted fragment was determined according to the aforementioned method and it was confirmed that the expected fusion gene was constructed.

The fusion gene of about 1.8 kb for transglutaminase having the pro-structure, which was ligated to the region encoding the N-terminal 25 amino acid residues (signal peptide) of the cell surface protein (SlpA) of *C. ammoniagenes* and which comprised the 5'-upstream region containing the promoter region of the gene of the protein corresponding to PS2 of *C. glutamicum* ATCC13869, was excised by digesting pVKSPTG1 with KpnI and XbaI, and the fragment was recovered using agarose electrophoresis. This fragment was inserted into KpnI-XbaI site of pPK4 described in JP-Kokai No. 9-322774 to construct pPKSTG1. Both plasmids, pVKSPTG1 and pPKSPTG1 contained the promoter derived from PS2 gene of *C. glutamicum*

(SEQ ID NO: 15)  5'-AAATTCCTGTGAATTAGCTGATTTAG-3'

(SEQ ID NO: 26)  5'-CGCAGCCAGCGATTTCATGCGTTTCATAGAGGCGAAGGCTCCTTGAATAGGT-3'

On the other hand, the primers shown in SEQ ID NO:27 and SEQ ID NO: 12 were synthesized based on the sequence of the transglutaminase fusion gene having the additional pro-structure part and the signal sequence of the cell surface protein (SlpA) of *C. ammoniagenes*. The region of the transglutaminase having the additional pro-structure part was then amplified by PCR method from pVSPTG1 obtained in Example 4(1) with the primers.

ATCC13869, the signal peptide gene derived from SlpA of *C. ammoniagenes* and the transglutaminase gene derived from *S. mobaraense*.

(3) Conversion to *E. coli* tac Promoter

The primers shown in SEQ ID NO:28 and SEQ ID NO:29 were synthesized based on the sequence of plasmid pKK223-3 (Amersham Pharmacia Co. Ltd.) into which *E. coli* tac promoter had been cloned. The region corresponding to tac promoter was amplified using PCR method from pKK223-3 DNA. The primer shown in SEQ ID NO:29 also comprises the sequence encoding the N-terminal amino acid sequence of the signal sequence of the cell surface protein (SipA) of *C. ammoniagenes* in order to construct the fusion gene having the pro-structure part, which contained the signal sequence of the cell surface protein (SlpA) of *C. ammoniagenes* (heterologously fused prepro-transglutaminase gene).

(SEQ ID NO: 12)  5'-CGCTCACATCACGGCCAGCCCTGCTTTACC-3'

(SEQ ID NO: 27)  5'-ATGAAACGCATGAAATCGCTGGCTGCGGCG-3'

(SEQ ID NO: 28)  5'-GGATCCGGAGCTTATCGACTGCACG-3'

(SEQ ID NO: 29)  5'-CGCAGCCAGCGATTTCATGCGTTTCATAATTCTGTTTCCTGTGTGAAATTGT-3'

SEQ ID NOs: 12 and 27: PCR primer

The fusion gene of transglutaminase having the pro-structure part, which was ligated to the region encoding the N-terminal 25 amino acid residues of the cell surface protein (SlpA) of *C. ammoniagenes* and to the 5'-upstream region containing the promoter region of the gene of the protein corresponding to PS2 of *C. glutamicum* ATCC13869, was then amplified by performing cross-over PCR with SEQ ID NO:15 and SEQ ID NO:12 using the mixture comprising 1

SEQ ID NOs:28 and 29: PCR primers

The fusion gene for transglutaminase having the additional pro-structure part, which was ligated to the region encoding the N-terminal 25 amino acid residues of the cell surface protein (SlpA) of *C. ammoniagenes* and which contained tac-promoter (heterologously fused prepro-transglutaminase gene), was amplified by performing cross-over PCR with SEQ ID NO:28 and SEQ ID NO:12 using the mixture of 1 µl of PCR solution of the amplified region corresponding to tac-promoter and 1 µl of PCR solution of the amplified region of the gene for transglutaminase having the pro-structure part, which contained the signal sequence of the cell surface protein (SlpA) of *C. ammoniagenes*, as the templates. The amplified fragment of about 1.5 kb was detected by agarose electrophoresis. This fragment was recovered from the agarose gel by EASYTRAP Ver. 2 (Takarashuzo Co. Ltd.) and inserted into SmaI site of the pVC7 as described in JP-Kokai No. 9-070291 to obtain pVTSPTG1. The nucleotide sequence of the inserted fragment was determined according to the aforementioned method and it was confirmed that the expected fusion gene was constructed.

The fusion gene about 1.5 kb for transglutaminase having the pro-structure part, which was ligated to the region encoding the N-terminal 25 amino acid residues of the cell surface protein (SlpA) of *C. ammoniagenes* and tac promoter, was excised by digesting pVTSPTG1 with KpnI and XbaI and was recovered using agarose electrophoresis. This fragment was inserted into KpnI-XbaI site of pPK4 described in JP-Kokai No.9-322774 to construct pPTSPTG1. Both plasmids pVTSPTG1 and pPTSPTG1 contained tac-promoter derived from *E. coli*, the signal peptide gene derived from SlpA of *C. ammoniagenes* and the pro-transglutaminase gene derived from *S. mobaraense*.

(4) Secretion of Pro-transglutaminase Using the Signal Sequence of Cell Surface Protein of *C. ammoniagenes*

*C. glutamicum* ATCC13869 was transformed with the constructed plasmid pVKSPTG1, pVTSPTG1, pPKSPTG1, or pPTSPTG1 and the strains grown on the CM2S agar medium comprising 5 mg/l of chloramphenicol or 25 mg/l of kanamycin were selected. The selected *C. glutamicum* ATCC13869 harboring pVKSPTG1, pVTSPTG1, pPKSPTG1, or pPTSPTG1 was then cultured in the aforementioned MM culture medium comprising 5 mg/l of chloramphenicol or 25 mg/l of kanamycin at 30° C. for 48 hours, respectively. After the culture was finished, 10 µl of the supernatant of the culture was subjected to SDS-PAGE and then Western blot was performed using anti-transglutaminase antibody as described in Biosci. Biotechnol. Biochem., 58, 82-87(1994) according to the conventional method. As a result, the similar amount of transglutaminase was confirmed to be secreted for either of the vectors, pVC7 or pPK4. The representative amounts of the secretion are shown in Table 2.

TABLE 2

The secreted amount of pro-transglutaminase using the signal sequence of cell surface protein of *C. ammoniagenes* ATCC13869

| plasmid | protransglutaminase (mg/l) |
|---|---|
| pPKSPTG1 | 102 |
| pPTSPTG1 | 74 |

Example 5

Secretory Production of Pro-transglutaminase Using the Fusion Gene Containing the Sequence Encoding the Signal Sequence of the Cell Surface Protein of *C. ammoniagenes* and the Protransglutaminase derived from *Streptoverticillium cinnamoneum* IFO12852

(1) Construction of the Fusion Gene Comprising the Sequence Encoding the Signal Sequence of the Cell Surface Protein of *C. ammoniagenes* and the Sequence Encoding the Pro-transglutaminase Derived from *S. cinnamoneum* IFO12852

The sequence of the transglutaminase gene of *S. cinnamoneum* IFO12852 has been determined [Japanese Patent Application No.11-295649]. The region from position 1 to position 32 in the amino acid sequence is presumed to be the sequence for the pre-part, from position 33 to position 86 is presumed to be the sequence for the pro-part and from position 87 to position 416 is presumed to be the sequence for the mature transglutaminase sequence. The nucleotide sequence and the entire amino acid sequence encoded by the nucleotide sequence are shown in SEQ ID NO:30 and SEQ ID NO:31. Additionally *Escherichia coli* AJ13669 which had been transformed with the plasmid pUJ-MTG containing the gene has been originally deposited in the National Institute of Bioscience and Human-Technology Agency of Industrial Science and Technology (Now, I Independent Administrative Agency, National Institute of Advance Industrial Science and Technology, Tsukuba Central 6, 1-1, Higashi 1-Chome Tsukuba-shi, Ibaraki-ken, 305-8566 Japan) on Oct. 14, 1999 as FERM P-17602 and has been transferred to the deposit under the Budapest Treaty on Aug. 28, 2000, and the deposit number of FERM BP-7287 has been allotted.

The region of 3.5 kb covering the full-length of the prepro-transglutaminase gene was firstly excised from pUJ-MTG with restriction enzyme BamHI, and pUCSCTG was generated wherein the region was inserted into BamHI site of pUC19.

Primers shown in SEQ ID NO:32 and SEQ ID NO:33 were synthesized, and the region of the gene comprising the pro-transglutaminase derived from *S. cinnamoneum* IFO12852 was amplified by PCR method using pUCSCTG as the template as previously described.

(SEQ ID NO: 32)  5'-GGC GAT GGG GAA GAG AAG GGG-3'

(SEQ ID NO: 33)  5'-GGC GGA TCC TVG CGT CGA GAG GCG TGG ACT GA-3'

SEQ ID NOs:32 and 33: PCR primers

The region, which contained the 5'-upstream region containing the promoter region of PS2 gene which is the cell surface protein of C. glutamicum and the region containing the signal sequence of the cell surface protein SlpA of C. ammoniagenes, was then amplified by performing PCR using the combination of SEQ ID NO:34 and SEQ ID NO:35 from pPKSPTG1 which was constructed in Example 4(2) as the template.

The primer shown in SEQ ID NO:35 also contained the sequence encoding the N-terminal amino acid sequence of pro-transglutaminase derived from Streptoverticillium cinnamoneum IFO12852 in order to construct the fusion gene with the transglutaminase derived from Streptoverticillium cinnamoneum IFO12852.

(SEQ ID NO: 34)  5'-TAC GAA TTC GAG CTC GGT ACC-3'

(SEQ ID NO: 35)  5'-CCC CTT CTC TTC CCC ATC GCC TGC CGT TGC CAC
                   AGG TGC GGC C-3'

SEQ ID NO: 34 and 35: PCR primers

The fragment of the heterologously fused prepro-transglutaminase gene, which was ligated to the signal sequence of the cell surface protein SlpA of C. ammoniagenes and the 5'-upstream region comprising the promoter region of PS2 gene, was amplified by performing cross-over PCR with SEQ ID NO: 34 and SEQ ID NO: 33 using the mixture comprising 1 µl of PCR solution of the amplified region encoding the gene for the pro-transglutaminase derived from C. cinnamoneum IFO12852 and 1 µl of PCR solution of the amplified region comprising 5'-upstream region containing the promoter region of the PS2 gene and the region containing the signal sequence of the cell surface protein SlpA of C. ammoniagenes, as the templates.

The amplified fragment of about 1.8 kb was detected by agarose electrophoresis. This fragment was digested with EcoRI and BamHI, and then recovered from the agarose gel and inserted into EcoRI-BamHI site of the pUC19 to obtain pUKSPTG2'. The sequence of the inserted fragment was determined according to the aforementioned method and it was confirmed that the fusion gene was constructed as expected. This pUKSPTG2' was digested with EcoRI and blunt-ended with Blunting Kit (Takarashuzo Co. Ltd.), and XbaI linker (Takarashuzo Co. Ltd.) having the sequence 5'-CTCTAGAG-3' wherein 5'-terminal was phosphorylated was then inserted and re-cyclized to construct pUKSPTG2. The fused preprotransglutaminase gene of about 1.8 kb (the protransglutaminase gene was derived from S. cinnamoneum IFO12852) was excised by digesting pUKSPTG2 with XbaI and was recovered using agarose electrophoresis. These fragments were inserted into XbaI site of pPK4 described previously to construct pPKSPTG2.

The preprotransglutaminase gene having a chimeric pro-structure part, wherein the N-terminal of the pro-structure part was partially replaced by the pro-structure part of S. mobaraense, was constructed (the mature transglutaminase gene and the part of the pro-structure part were derived from S. cinnamoneum IFO12852).

First, the fragment of about 1.8 kb containing the preprotransglutaminase gene of EcoRI-BamHI was excised from the plasmid pPKSPTG1 (for the expression of the pro-transglutaminase derived from S. mobaraense IFO13819) which was constructed in Example 4(2), and the fragment was inserted into EcoRI-BamHI site of pUC19 (pUK-SPTG1). The fragment of about 1.2 kb was excised by digesting pUKSPTG1 with AatII, and pUKSPTG2' was also digested with AatII to prepare the fragment of about 3.3 kb removing the fragment of about 1.2 kb. This fragment of about 3.3 kb was ligated to the AatII fragment of about 1.2 kb derived from pUKSPTG1, and clones wherein the AatII fragment was inserted were selected according to the conventional genetic engineering techniques. In order to determine the orientation the inserted AatII fragment in the clones, the clones were serially sequenced and the clones where the fragment was inserted in the desired orientation (for encoding preprotransglutaminase) were selected (pUKSPTG3').

Moreover the EcoRI site of pUKSPTG3' was also blunt-ended as described for pUKSPTG2' and XbaI linker was inserted to construct pUKSPTG3. Further the 1.8 kb XbaI fragment excised from pUKSPTG3 was inserted into XbaI site of pPK4 to construct pPKSPTG3.

(2) Secretion of the Protransglutaminase Derived from Streptoverticillium cinnamoneum IFO12852 Using the Signal Sequence of the Cell Surface Protein from C. ammoniagenes C. glutamicum ATCC13869 was transformed with the plasmid pPKSPTG2 or pPKSPTG3, and the strains which grew on the CM2S agar medium described above comprising 25 mg/l of kanamycin were selected. The selected C. glutamicum ATCC13869 harboring pPKSPTG2 or pPKSPTG3 was then cultured respectively in MMTG liquid culture medium (60 g of glucose, 0.4 g of magnesium sulfate heptahydrate, 30 g of ammonium sulfate, 1 g of potassium dihydrogenphosphate, 0.01 g of ferrous sulfate heptahydrate, 0.01 g of manganese (II) sulfate pentahydrate, 450 µg of thiamine hydrochloride, 450 µg of biotin, 0.15 g of DL-methionine, 50 g of calcium carbonate per liter of distilled water, adjusted to pH 7.5) containing 25 mg/l of kanamycin at 30° C. for 3 days. After the culture was completed, 10 µl of the supernatant of the culture was subjected to SDS-PAGE and then Western blot analysis was performed according to the conventional method with anti-transglutaminase antibody as previously described. This antibody was an antibody for the transglutaminase derived from S. mobaraense, but it also showed the reactivity to the transglutaminase derived from S. cinnamoneum. Consequently the secretion of the transglutaminase having the pro-structure part derived from S. cinnamonieum IFO12852 was confirmed (about 30 to 50 mg/l).

Example 6

Cloning of the Serine Protease (SAMP45) Gene, and the Construction and Evaluation of Expression Plasmids (1) Construction of the Serine Protease (SAMP45) Gene having the Pro-structure Part and the Signal Sequence of the Cell Surface Protein of C. ammoniagenes (Heterologously Fused Prepro-Serine Protease (SAMP45) Gene)

The sequence of the gene of SAMP45 which is a serine protease produced by S. albogriseolus [J. Bacteriol., 179, 430-438(1997)] has already been determined. The primers shown in SEQ ID NO:36 and SEQ ID NO:37 were synthesized on referring to this sequence and the gene region containing the N-terminal pro-structure part of SAMP45, mature SAMP45 and the C-terminal pro-structure part was amplified using PCR method according to the method described previously.

(SEQ ID NO: 36)  5'-AACGGGGAGAACAGCACGGCCGCCGG-3'

(SEQ ID NO: 37)  5'-GGCGAATTCTCCGGCGGGCCGTCACCGGT-3'

SEQ ID NOs:36 and 37: PCR primer

The region comprising 5'-upstream region containing the promoter region of the gene of the cell surface protein PS2 from *C. glutamicum* and the signal sequence of the cell surface protein SlpA from *C. ammoniagenes* was similarly amplified using PCR method with the combination of SEQ ID NO:38 and SEQ ID NO:39 using pPKSPTG1 constructed in Example 4(2) as the template.

The primer shown in SEQ ID NO:39 comprises the sequence encoding the N-terminal amino acids of pro-serine protease in order to construct the fusion gene containing the serine protease having the pro-structure part.

(SEQ ID NO: 38)  5'-GGCAAGCTTAAATTCCTGTGAATTAGCTGA-3'

(SEQ ID NO: 39)  5'-CGGCCGTGCTGTTCTCCCCGTTTGCCGTTGCCACAGGTGCGGCC-3'

SEQ ID NO:38 and 39: PCR primers to construct the fused pro-serine protease gene Then the gene fragment of the heterologously fused prepro-serine protease gene, which was ligated to the signal sequence of the cell surface protein SlpA of *C. ammoniagenes* and to the 5'-upstream region containing the promoter region of PS2 gene, was amplified by performing cross-over PCR with SEQ ID NO:38 and SEQ ID NO:37 using the mixture, as the templates, which comprises 1 µl of PCR solution of the amplified region comprising the gene for the N-terminal pro-structure of SAMP45, mature SAMP45 and the C-terminal pro-structure, and 1 µl of PCR solution of the amplified region comprising the 5'-upstream region containing the promoter region of the PS2 gene and the signal sequence of the cell surface protein SlpA of *C. ammoniagenes*, respectively.

The amplified fragment of about 3.9 kb was detected by agarose gel electrophoresis. The PCR product was digested with HindIII and EcoRI, then subjected to agarose gel electrophoresis, and the fragment of about 3.9 kb was recovered from agarose gel and inserted into HindIII-EcoRI site of the aforementioned pVC7 to obtain pVSS1, respectively. The sequence of the inserted fragment was determined according to the aforementioned method and it was confirmed that the fusion gene was constructed as expected.

(2) Secretion of the Serine Protease using the Signal Sequence of the Cell Surface Protein of *C. ammoniagenes*

*C. glutamicum* ATCC13869 was transformed with the plasmid pVSS1 and the strains which grew on the CM2S agar medium described above comprising 5 mg/l chloramphenicol were selected. The selected *C. glutamicum* ATCC13869 harboring pVSS1 was then cultured in MMTG culture medium comprising 5 mg/l chloramphenicol at 30° C. for 70 hours. 1 ml of the culture medium was separate into the supernatant of the culture medium and the cells by centrifugation. The cells were suspended in 0.1 M sodium phosphate buffer (pH 7.0). The activity of the serine protease was determined as follows: 50 µl of the supernatant of the culture medium or the cell suspension was added to 20 mM sodium phosphate buffer (pH 7.0) containing 0.25 mM Bz-Phe-Val-Arg-pNA (Bachem Co. Ltd.) to give a total amount of 0.6 ml, which was maintained at 30° C. for 20 minutes. Thereafter the reaction was terminated upon the addition of 0.4 ml of 50% acetic acid. The absorbance was measured at 410 nm and the amount of p-NA (p-nitroanillide) released was measured to determine the activity. One unit of the enzyme was defined as the amount of enzyme which releases 1 µmol of pNA per one minute. As a result, the activity of serine protease was not detected in the supernatant of the culture medium, but was detected in the cell suspension. Calculating from the values of detected activity and the values of the specific activity reported in the literature [J. Bacteriol., 179, 430-438(1997)], as much as about 9 mg/l of serine protease was confirmed to be expressed and secreted at the surface of the cell.

Example 7

Cloning of the Proline Specific Peptidase (svPEP) Gene, and Construction and Evaluation of Expression Plasmids (1) Purification and Analysis of the N-terminal Amino Acids of the Proline Specific Peptidase (svPEP) Produced by *S. mobaraense* IFO13819

800 mL of ISP2 liquid culture medium (4 g of yeast extract, 10 g of malt extract, 4 g of glucose filled up to IL by water, adjusted to pH 7.3) was placed in a 5L Sakaguchi flask and *S. mobaraense* IFO13819 was inoculated from the plate into the flask and cultured by shaking the flask at 30° C. for 48 hours at 120 rpm.

The culture medium was centrifuged to remove the supernatant of the culture and the cells were harvested. After washing the cells with 20 mM Tris-HCl buffer containing 25 mg/l kanamycin, the resulting cells were suspended in 0.1 M sodium phosphate buffer (pH 7.0) containing 25 mg/l kanamycin. The suspension was shaken on ice for 4 hours and centrifuged to give the supernatant, which was collected. After the supernatant was filter-sterilized using nitrocellulose filter (0.22 µm pore sized, Sartrius Co. Ltd.), the supernatant was passed through the Butyl-Sepharose 4FF (Amersham Pharmacia Co. Ltd.) column (1.6φ×10 cm), which had been pre-equilibrated with 1.5 M ammonium sulfate/50 mM phosphate buffer (pH 7.0), using FPLC (Amersham Pharmacia Co. Ltd.) and eluted by the linear gradient of ammonium sulfate 1.5 to 0 M in the same buffer. Fractions containing active components were pooled and passed through Phenyl-Sepharose HP column (1 mL, Amersham Pharmacia Co. Ltd.) under the same condition, and the active fractions were pooled and dialyzed overnight against 50 mM sodium phosphate buffer (pH 7.0) at 4° C. to give partially purified enzyme solution. The partially purified enzyme solution was subjected to a reversed phase chromatography for further purification. The condition of the reversed phase chromatography was as follows:
HPLC device: pump: HITACHI L-6300, detector: L-4000H
Column: PROTEIN C4 214TP5410(VYDAC Co. Ltd.)
Elution: Elution was effected by a lineal gradient of acetonitrile 24-40%/0.1% trifluoroacetic acid (20 min) at room temperature
Flow rate: 1.0 ml/min.
Detection wavelength: 280 nm The enzyme sample which was purified under the condition describe above was transferred onto Polyvinylidene-difluoride (PVDF) membrane using Membrane Cartridge (Perkin Elmer Co. Ltd.) and the N-terminal amino acid sequence was analyzed using gas-phase Protein Sequencer PPSQ-10 (Shimazu Seisakusho Co., Ltd.).

As a result, the N-terminal 20 amino acid residues were determined, which are shown in SEQ ID NO:40.

SEQ ID NO:42: a probe for svPEP

The nucleotide sequence of the fragment which was cloned as pUMP1 was determined. The amino acid sequence encoded by this gene was deduced and the previously determined N-terminal amino acid sequence (20 residues) based on the enzyme protein was found, and the entire primary amino acid sequence containing the putative signal sequence and the pro-structure part of svPEP was determined, which is shown in SEQ ID NO:9. In the amino acid sequence, position 1 to 25 is supposed to be the signal sequence, position 26 to 33 is supposed to be the pro-structure and position 34 to 477 is the mature svPEP.

*Escherichia coli* AJ13669 which was transformed with pUMP1 has been deposited in the National Institute of Bioscience and Human-Technology Agency of Industrial Science and Technology (Now, Independent Administrative Agency, National Institute of Advance Industrial Science and Technology, Tsukuba Central 6, 1-1, Higashi 1-Chome

```
(SEQ ID NO: 40)  Gln Ala Asp Ile Lys Asp Arg Ile Leu Lys Ile Pro
                  1               5                   10

Gly Met Lys Phe Val Glu Glu Lys
                                  15                  20
```

(2) Acquisition of the Proline-Specific Peptidase (svPEP) Gene Derived from *S. mobaraense* IFO13819

The region which is deduced from the determined N-terminal amino acid sequence of svPEP and which has less degeneracy, Lys-Ile-Pro-Gly-Met-Lys-Phe-Val-Glu-Glu-Lys (SEQ ID NO:41), was selected and the synthetic oligonucleotide shown in SEQ ID NO: 42 was generated. The chromosomal DNA of *S. mobaraense* IFO13819 prepared according to the conventional method was digested with various restriction enzymes which recognize 6-nucleotides sequence and then analyzed by Southern blot hybridization method using this synthetic oligonucleotide as the probe and thereby a single band of about 6 kb was detected by SacI cleavage.

Accordingly, the chromosomal DNA of *S. mobaraense* IFO13819 prepared according to the aforementioned method was digested with Sac I and the fragment of about 6 kb was recovered by agarose gel electrophoresis using EASYTRAP Ver. 2 (Takarashuzo Co. Ltd.). The recovered fragment was inserted in Sac I site of pUC18, which was introduced into the competent cell of *Escherichia coli* JM109 (Takarashuzo Co. Ltd.), thereby producing a library. The generated library in this way was screened for the strain which harbored the plasmid where the fragment of svPEP gene was cloned, by screening the library through colony hybridization using $^{32}$P-labeled synthetic oligonucleotide shown in SEQ ID NO:38 as a probe to obtain the intended gene. The plasmid recovered from this strain was designated as pUMP1.

Tsukuba-shi, Ibaraki-ken, 305-8566 Japan) on May 15, 2000 as FERM BP-7160 under the Budapest Treaty.

(3) Construction of the Proline Specific Peptidase (svPEP) Gene Having the Pro-structure Part with the Signal Sequence of the Cell Surface Protein of *C. ammoniagenes* (Heterologously Fused Prepro-Proline Specific Peptidase (svPEP) Gene)

Primers shown in SEQ ID NO:43 and SEQ ID NO:44 were synthesized on referring to the sequence of svPEP determined in Example 7(2), and the gene region containing the pro-part of svPEP and mature svPEP were amplified by PCR method in the same manner as described previously using pUMP1 constructed in Example 7(2) as the template.

(SEQ ID NO: 43) 5'-GAGGCGGCGTCGATCACCGCCCC-3'

(SEQ ID NO: 44) 5'-GCCAAGCTTGAAGCACCGGGCGGCGGCACCCGG-3'

SEQ ID NO: 43 and 44: PCR primers

Then the region, which comprises the 5'-upstream region containing the promoter region of PS2 gene which is the gene of the cell surface protein of *C. glutamicum* and the region containing the signal sequence of the cell surface protein SlpA of *C. ammoniagenes*, was amplified by PCR method from pPKSPTG1 constructed in Example 4(2) as the template using the combination of SEQ ID NO:38 and SEQ ID NO:45.

The primer shown in SEQ ID NO:45 comprises the sequence encoding the N-terminal amino acids of svPEP in order to construct the fusion gene fused to the svPEP having the pro-structure part.

(SEQ ID NO: 42) 5'-AAGATCCCCGGGATGAAGTTCGTCGAGGAG AAG-3'

(SEQ ID NO: 5'-GGCAAGCTTAAATTCCTGTGAATTAGGCTGA-3'
38)

(SEQ ID NO: 5'-GGGGCGGTGATCGACGCCGCCTCTGCCGTTGCCACAGGTGCGGCCA-3'
45)

The fragment of the heterologously fused gene of prepro-svPEP, which was ligated to the signal sequence of the cell surface protein SlpA of *C. ammoniagenes* and the 5'-upstream region containing the promoter region of PS2 gene, was then amplified by performing cross-over PCR with SEQ ID NO:38 and SEQ ID NO:44 using the mixture, as the templates, which comprises 1 µl of each PCR solution of the region containing the gene encoding the pro-structure part of svPEP and the mature svPEP, which were amplified respectively, and 1 µl of PCR solution of the amplified region comprising 5'-upstream region containing the promoter region of the PS2 gene and the signal sequence of the cell surface protein SlpA of *C. ammoniagenes*.

(SEQ ID NO: 5'-GGCAAGCTTAAATTCCTGTGAATTAGCTTA-3'
38)

(SEQ ID NO: 5'-GCCAAGCTTGAAGCACCGGCGGCGGCACCCGG-3'
44)

SEQ ID NO:38 and SEQ ID NO 44: PCR primer

The amplified fragment of about 2.1 kb was detected by agarose gel electrophoresis. The PCR fragment was digested with HindIII, and then subjected to agarose gel electrophoresis and the fragment of about 2.1 kb recovered from the agarose gel and inserted into the HindIII site of the pVSS1 described in Example 6(1) to obtain pVSSSP1, respectively. The sequence of the inserted fragment was determined according to the conventional method and it was confirmed that the expected fusion gene was constructed.

(4) Secretion of the Proline Specific Peptidase Using the Signal Sequence of the Cell Surface Protein of *C. ammoniagenes*

*C. glutamicum* ATCC13869 was transformed with the constructed plasmid pVSSSP1 and the strains which grew on the CM2S agar medium described above comprising 5 mg/l chloramphenicol were selected. The selected *C. glutamicum* ATCC13869 harboring pVSSSP1 was then cultured in MMTG culture medium, described above, comprising 5 mg/l chloramphenicol at 30° C. for 70 hours. 10 ml of the supernatant of the culture was separated by centrifugation into the supernatant of the culture medium and the cells. The cells were suspended in 0.1 M sodium phosphate buffer (pH 7.0). The activity of svPEP was determined as follows: 50 µl of the supernatant of the culture medium or the cell suspension was added to 20 mM sodium phosphate buffer (pH 7.0) containing 0.25 mM Ala-Ala-Pro-pNA (Bachem Co. Ltd.) to give a total amount of 0.6 ml and the mixture was maintained at 30° C. for 20 minutes. Thereafter the reaction was terminated upon the addition of 0.4 ml of 50% acetic acid. The absorbance was measured at 410 nm and the amount of p-NA (p-nitroanillide) released was calculated to determine the activity. One unit of the enzyme is defined as the amount of enzyme which releases 1 µmol of pNA per 1 minute. As a result, the activity of svPEP was not detected in the supernatant of the culture medium, but was detected in the cell suspension. Calculating from the values of the detected activity and the values of the specific activity (35.5 u/mg) described in Example 7(1), as much as about 50 mg/l of svPEP was confirmed to be expressed and secreted at the surface of the cell.

(5) Cleavage of the Pro-structure Part of the Transglutaminase having the Pro-structure by the Serine Protease and the Proline Specific Protease Expressed and Secreted by *C. glutamicum* ATCC13869

*C. glutamicum* ATCC13869 harboring the secretory expression plasmid pPKSPTG1 for transglutaminase having the pro-structure part described in Example 4(2) was transformed with the constructed plasmid pVSSSP1, and the strains grown on the aforementioned CM2S agar medium comprising 5 mg/l of chloramphenicol and 25 mg/l kanamycin were selected. Then the selected *C. glutamicum* ATCC13869 harboring pVSSSP1 and pPKSPTG1 was cultured in MMTG culture medium, described above, comprising 5 mg/l chloramphenicol and 25 mg/l kanamycin at 30° C. for 70 hours.

After the culture was finished, 10 µl of the supernatant of the culture was subjected to SDS-PAGE and then Western blot analysis was performed with anti-transglutaminase antibody previously described according to the conventional method. As a result, it was confirmed that SAMP45 and svPEP were normally expressed and secreted, and that the pro-structure part was cleaved from the transglutaminase having the pro-structure part which had been also secreted, thereby the secretion of the transglutaminase having the similar molecular weight to that of the naturally occurring mature transglutaminase was confirmed.

The transglutaminase activity was tested for the supernatant by the hydroxamate method previously described, which confirmed that it contained the similar specific activity (about 20 U/mg) to that of the naturally occurring transglutaminase.

Additionally, it was semi-dry blotted onto polyvinylidene difluoride (PVDF) membrane according to the method previously described after SDS-PAGE. After blotting, the PVDF membrane was stained with Coomassie Brilliant Blue, de-stained and air-dried. The portion containing the mature transglutaminase was excised and analyzed for the N-terminal amino acid sequence using a protein sequencer. As a result, it was confirmed that it had the same N-terminal sequence as the naturally occurring transglutaminase derived from *S. mobaraense* starting Asp located at position 77, which is shown in SEQ ID NO:6.

Example 8

Secretory Production of Human Epidermal Growth Factor (hEGF) Using the Fusion Gene Containing the Sequence Encoding the Signal Sequence of the Cell Surface Protein from *Corynebacterium ammoniagenes* ATCC6872 and the Sequence Encoding Human Epidermal Growth Factor (1) Construction of hEGF Gene Containing the Signal Sequence of the Cell Surface Protein of *Corynebacterium glutamicum* ATCC13869

The sequence of the gene of the cell surface protein of *Corynebacterium glutamicum*, PS2, has been already determined [Mol. Microbiol., 9, 97-109 (1993)]. The primers shown in SEQ ID NO:46 and NO:47 were synthesized on referring to this sequence. The gene region comprising the 5'-upstream region and the region encoding N-terminal 44 amino acids residue of the protein correspond to PS2 was amplified using PCR method from the chromosomal DNA of *Corynebacterium glutamicum* ATCC13869 which had been prepared according to the method of Saito & Miura [Biochem. Biophys. Act., 72, 619 (1963)]. The primer shown as SEQ ID NO:46 contained KpnI site at its 5'-terminal which was required to insert the region into a plasmid.

(SEQ ID NO: 46)   5'-CTCGGTACCCAAATTCCTGTGAATTAGCTGATTTAG-3'

(SEQ ID NO: 47)   5'-GTTGAAGCCGTTGTTGATGTTGAA-3'

SEQ ID NOs:46 and 47: PCR primer

On the other hand, the primers shown in SEQ ID NO:48 and NO:49 were synthesized. The region encoding hEGF was amplified by PCR method from plasmid pT13SΔhIL2-KS-hEGF (H3) (JP Kokai No. 64-2583) which contains the gene sequence for hEGF. *Escherichia coli* AJ12354 transformed with plasmid pT13SΔhIL2-KS-hEGF(H3) containing the gene was originally deposited at Independent Administrative Agency, National Institute of Advance Industrial Science and Technology (Tsukuba Central 6, 1-1, Higashi 1-Chome Tsukuba-shi, Ibaraki-ken, 305-8566 Japan) on Nov. 20, 1987 and has been transferred to the international deposit under the Budapest Treaty on Mar. 18, 2002, and the deposit number of FERM BP-7966 has been allotted.

The primer shown as SEQ ID NO:48 contains the sequence encoding the C-terminal amino acids of the signal sequence of PS2 in order to construct the fusion gene with the region which comprises 5'-upstream region and which also comprises the region encoding 44 N-terminal amino acid residues of the protein corresponding to PS2.

Sequencer 373A (PE Applied Biosystems) to confirm that the expected fusion gene had been constructed.

(2) Construction of hEGF Gene Containing the Signal Sequence of *Corynebacterium ammoniagenes* ATCC6872

The primers shown in SEQ ID NO:24 and SEQ ID NO:50 were synthesized on referring to the sequence of the gene of the cell surface protein (SlpA) [JP-Kokai No. 10-108675] of *C. ammoniagenes* and the region comprising the 5'-upstream region containing the promoter region of the cell surface protein (SlpA) gene and the region encoding its N-terminal 25 amino acid residues was amplified using PCR method from the chromosomal DNA of *C. ammoniagenes* prepared according to the method described in Example 8(1). The primer shown in SEQ ID NO:50 also contained the sequence encoding the N-terminal amino acids of hEGF in order to construct the fusion gene fused with hEGF.

(SEQ ID NO: 24)   5'-GCCCAGAAGCCCAAAATTGAGATTT-3'

(SEQ ID NO: 50)   5'-AGGGCACTCAGAATCGGAATTTGCCGTTGCCACAGGTGCGGCC-3'

The primers indicated in SEQ ID NO:51 and SEQ ID NO:49 were synthesized and the region encoding hEGF was amplified from plasmid pT13SDhIL2-KS-hEGF(H3) (JP Kokai No. 64-2583) containing hEGF gene sequence.

(SEQ ID NO: 49)   5'-CGGCCACGATGCGTCCGGCG-3'

(SEQ ID NO: 51)   5'-AATTCCGATTCTGAGTGCCCT-3'

(SEQ ID NO: 48)   5'-AACATCAACAACGGCTTCAACAATTCCGATTCTGAGTGCCCT-3'

(SEQ ID NO: 49)   5'-CGGCCACGATGCGTCCGGCG-3'

Then, the fusion gene, where hEGF was ligated to the region comprising 5'-upstream region and the region encoding N-terminal 44 amino acid residues of the cell surface protein of *Corynebacterium glutamicum*, was amplified by performing cross-over PCR with SEQ ID NO:46 and SEQ ID NO:49 using the mixture, as the template, containing 1 μl of PCR reaction solution with the region comprising 5'-upstream region and the region encoding N-terminal 44 amino acid residues of the cell surface protein of *Corynebacterium glutamicum* and 1 μl of PCR reaction solution containing amplified hEGF gene region. The fragment of about 0.9 kb was detected by agarose gel electrophoresis. The fragment was recovered from agarose gel by using EASY TRAP Ver. 2 (Takar4ashuzo Co. Ltd.). The recovered DNA was cleaved by KpnI and BamHI (Takar4ashuzo Co. Ltd.), purified by DNA Clean-UP system (Promega), and inserted to KpnI-BamHI sited of plasmid pPK4 described in JP Kokai No. 9-322774 to obtain pPKEGF. The nucleotide sequence of the inserted fragment was determined by using Dye Terminator Cycle Sequencing kit (PE Applied Biosystems) and DNA SEQ ID NOs: 49 and 51: PCR primer The fusion gene, where hEGF gene was ligated to the 5'-upstream region and the region encoding the N-terminal 25 amino acid residues of the cell surface protein (SlpA) of *C. ammoniagenes*, was amplified by performing cross-over PCR with SEQ ID NO:49 and SEQ ID NO:24 using the mixture, as the templates, containing 1 μl of PCR solution of the amplified 5'-upstream region and the region encoding the N-terminal 25 amino acid residues of the cell surface protein (SlpA) of *C. ammoniagenes* and 1 μl of PCR solution for hEGF gene region.

Additionally, the primers indicated in SEQ ID NO:52 and SEQ ID NO:53 were synthesized, and 5'-upstream region of the protein corresponding to PS2 was amplified by PCR method using the plasmid pKEGF obtained in Example 8 (1) as the template. The primer shown in SEQ ID NO:53 contained the 3'-terminal sequence of 5'-upstream region for the protein corresponding to PS2 and the region encoding the N-terminal amino acids of the signal sequence of the cell surface protein (SlpA) from *Corynebacterium ammoniagenes*.

```
(SEQ ID NO: 52)  5'-GAATTCGAGCTCGGTACCCA-3'

(SEQ ID NO: 53)  5'-AGCGATTTCATGCGTTTCATAGAGGCGAAGGCTCCTTGAA-3'
```

On the other hand, the gene hEGF gene region containing the signal sequence of the cell surface protein (SlpA) from *Corynebacterium ammoniagenes* was amplified by using the primers indicated in SEQ ID NO:54 and SEQ ID NO:49 prepared based on the hEGF fusion gene comprising the signal sequence and the 5'-upstream region of the cell surface protein (SlpA) from *Corynebacterium ammoniagenes*. For PCR, Pyrobest DNA polymerase (Takarashuzo Co. Ltd.) was used and the reaction condition followed the instructed protocol.

```
(SEQ ID NO: 49)    5'-CGGCCACGATGCGTCCGGCG-3'

(SEQ ID NO: 54)    5'-ATGAAACGCATGAAATCGCTGGC-3'
```

The fusion gene of hEGF, which was ligated to the region encoding the N-terminal 25 amino acid residues of the cell surface protein (SlpA) of *Corynebacterium ammoniagenes* and to the 5'-upstream region encoding the protein corresponding to PS2 of *Corynebacterium glutamicum*, was then amplified by performing cross-over PCR with SEQ ID NO:52 and SEQ ID NO:49 using the mixture comprising 1 µl of PCR solution of the amplified 5'-upstream region for the protein corresponding to PS2 of *Corynebacterium glutamicum* and 1 µl of PCR solution of the amplified region of the gene for hEGF having the signal sequence of the cell surface protein (SlpA) of *Corynebacterium ammoniagenes*. For PCR, Pyrobest DNA polymerase (Takarashuzo Co. Ltd.) was used and the reaction condition followed the instructed protocol. The amplified fragment of about 0.9 kb was detected by agarose gel electrophoresis. This fragment was recovered from the agarose gel using EASYTRAP Ver. 2 (Takarashuzo Co. Ltd.), digested with KpnI and BamHI (Takarashuzo Co. Ltd.) and was purified with DNA Clean-UP system (Promega). The fragment was inserted into KpnI-BamHI site of the plasmid pPK4 described in JP Kokai No. 9-322774 to obtain pPSEGF. The nucleotide sequence of the inserted fragment was determined by using Dye Terminator Cycle Sequencing kit (PE Applied Biosystems) and DNA Sequencer 373A (PE Applied Biosystems) to confirm that the expected fusion gene had been constructed.

(3) Generation of hEGF Producing Strains

*Corynebacterium glutamicum* ATCC 13869 was transformed with the hEGF expression plasmid pPSEGF constructed in (2) by electroporation method to obtain kanamycin resistant strains. The obtained strains was cultured with shaking at 30° C. for 3 days with MMTG liquid medium (60 g of glucose, 0.4 g of magnesium sulfate heptahydrate, 30 g of ammonium sulfate, 1 g of potassium dihydrogenphosphate, 0.01 g of ferrous sulfate heptahydrate, 0.01 g of manganese(II) sulfate pentahydrate, 450 µg of thiamine hydrochloride, 450 µg of biotin, 0.15 g of DL-methionine, 50 g of calcium carbonate per liter of distilled water, adjusted to pH 7.5) containing 25 mg/ml of kanamycin. The cells were removed by centrifugation and 10 µl of the supernatant of the culture was subjected to SDS-PAGE. The commercially available hEGF (PEPRO TECHEC LTD) was simultaneously subjected to electrophoresis as a standard, and Coomassie Brilliant Blue (CBB) staining was carried out. The results showed that the band was detected at the position corresponding to the same mobility as the standard. There were few other impure proteins in the culture supernatant.

(4) Determination of the Amount of hEGF Produced by the hEGF Producing Strain Harboring the Plasmid pPSEGF The culture supernatant of the hEGF producing strain was analyzed with HPLC column (YMC-AP203Ca300A.C18, particle size 5 µm, diameter 4.6 mm×length 250 mm), using 0.1% TFA/24% acetonitrile, 0.1% TFA/44 acetonitrile as buffers, 1%/min. linear gradient, flow rate 1.0 ml/min and detection at 280 nm. The quantification was carried out by comparing the peak area with the area observed when the hEGF standard was analyzed, which revealed the value of about 100 mg/L.

(5) Determination of the Biological Activity of hEGF Secreted by hEGF Producing Strain Harboring the Plasmid pPSEGF The EGF activity in the culture supernatant of the hEGF producing strain was determined. MCF-7 cells (A. V. Krishman, Journal of Bone and research, 6, 1099-1107, 1991) were placed on 96-well plate at a initial cell density of $1 \times 10^4$ per well and the 2-fold serial dilution of the culture supernatant of the EGF producing strain was added to the wells. The uptake of thymidine was determined after 72 hours. The activity was $1.4 \times 10^9$ U/ml as calculated by comparing with the value of hEGF standard, $10^7$ U/mg.

(6) Analysis of N-terminal Amino Acid Sequence of hEGF Secreted by the hEGF Producing Strain Harboring the Plasmid pPSEGF 120 µl of the culture supernatant of hEGF producing strain was applied to HPLC column, and isolated by using the condition described for quantification by HPLC. The peak corresponding with the elution position of the standard hEGF was collected. The determination was carried out by using gas phase amino acid sequencer PPSQ-10 (Shimadzu Co.). The results are as follows: Asn for the first residue; Ser for the second residue; Asp for the third residue; Ser for the fourth residue, respectively from the N-terminal. The results corresponded to the N-terminal amino acid sequence of hEGF indicated in SEQ ID NO:55.

(7) Determination of the Molecular Weight of hEGF Secreted by the hEGF Producing Strain Harboring the Plasmid pPSEGF 120 µl of the culture supernatant of hEGF producing strain was applied to HPLC column, and isolated by using the condition described in (4).

The eluted hEGF peak was collected. The sample was applied again to the same HPLC for fractionation, which confirmed that the sample exhibited one peak in HPLC. The sample was subjected to mass spectroscopy. The determination was carried out by using MALDI-TOFMS (Matrix assisted laser deionization—time of flight mass spectrometer) MALDI IV (Shimadzu Co.). The average of two measurements was 6176. The result was within the limit of error of theoretical value 6217 which had been calculated for the molecular weight of hEGF, assuming that there were three S—S bonds in the molecule. Thus, hEGF produced by the EGF producing strain prepared by the described method was confirmed to have the expected amino acid sequence and structure.

Example 9

Construction of *Corynebacterium glutamicum* AJ12036 Improved in the Secretion of Heterologous Proteins, Construction of Cell Surface Protein (PS2) Gene Disruption Strain Derived from AJ12036, and the Estimation of the Production of Heterologous Protein Using these Mutant Strains (1) Production of Cell Surface Protein (PS2) Gene Disruption Strain from *Corynebacterium glutamicum* AJ12036

Streptomycin (Sm) resistant strain AJ12036 had been bred from *Corynebacterium glutamicum* ATCC13869 and AJ12036 has been used as a host for gene recombination with *Corynebacterium glutamicum* (U.S. Pat. No. 4,822,738). *Corynebacterium glutamicum* (formerly, *Brevibacterium lactofermentum*) AJ12036 was deposited on the National Institute of Microbial Technology, Agency of Industrial Science and Technology (Now, Independent Administrative Agency, National Institute of Advance Industrial Science and Technology, Tsukuba Central 6, 1-1, Higashi 1-Chome Tsukuba-shi, Ibaraki-ken, 305-8566 Japan) on Mar. 26, 1984 as FERM BP-734.

Since it was revealed that AJ12036 strain slightly secreted the cell surface protein (PS2) into the culture medium, it was supposed that the secretion efficiency of proteins could be further improved by conducting the gene disruption such that it would become completely defective in producing PS2. Therefore, the complete PS2 gene defective strain was constructed using homologous recombination as described below.

The primers described below were synthesized on referring the chromosomal DNA of *Corynebacterium glutamicum* ATCC13869 prepared according to the method of Saito and Miura [Biochim. Biophys. Acta., 72, 619 (1963)] and PCR was carried out with the combination of SEQ ID NOs:56 and 57, and SEQ ID NOs:58 and 59. The sequence of PS gene of *Corynebacterium glutamicum* ATCC13869 was described in U.S. Pat. No. 5,547,864, and a part of the coding region and its 5'-upstream gene sequence were described in SEQ ID NO:4.

Crossover-PCR with the amplified each fragment and the combination of the primers of SEQ ID NO:56 and NO:59 was conducted to amplify ΔPS2 fragment where the promoter region and the N-terminal region of the coding region of PS2 gene were deleted from PS2 gene. This fragment was cloned into SmaI site of pUC19 to construct pUΔPS2. pUΔPS2 was digested with KpnI and XbaI to excise ΔPS2 fragment and, pHSΔPS2 was constructed by inserting the fragment into KpnI-XbaI site of pHS4 (U.S. Pat. No. 5,616,489) which is a temperature sensitive plasmid vector derived from pHM1519. *Escherichia coli* AJ12570 transformed with the plasmid pHS4 was deposited in National Institute of Bioscience and Human-Technology, Agency of Industrial Science and Technology, Ministry of International Trade and Industry (Now, Independent Administrative Agency, National Institute of Advance Industrial Science and Technology, Tsukuba Central 6, 1-1, Higashi 1-Chome Tsukuba-shi, Ibaraki-ken, 305-8566 Japan) on Oct. 11, 1990 as FERM BP-3523.

(SEQ ID NO:56) 5'-act ggg agg cta tct cca tt-3'
(SEQ ID NO:57) 5'-atc gat ctg atc acg tta α-3'
(SEQ ID NO:58) 5'-tgt aac gtg atc aga tcg att cac tgg tcg aca ccg ttg a-3'
(SEQ ID NO:59) 5'-acg gaa gct acc ttc gag gt-3'
SEQ ID NO:56 to SEQ ID NO:59: PCR primer pHSΔPS2 was introduced into AJ12036 by electroporation, and the complete PS2 gene defective strain was obtain by homologous recombination described in Japanese Patent No.2763054. This strain was designated as YDK010 strain.

(2) Estimation of Secretory Production of Heterologous Proteins Using *Corynebacterium glutamicum* AJ12036 and Cell Surface Protein (PS2) Gene Disruption Strain Derived from AJ12036

The protransglutaminase expression plasmid pPKSPTG1, which was described in Example 4 (2), was introduced into AJ12036 and YDK010 strains to obtain the transformants. These transformants and the control strain obtained by introducing pPKSPTG1 into the wild type *Corynebacterium glutamicum* ATCC13869, were used to estimate the amount of secretory production.

Similarly, the amount of secretory production was estimated for SAMP45 secretory expression plasmid pVSS1, for svPEP secretory expression plasmid pVSSSP1 and for hEGF secretory expression plasmid pPSEGF after obtaining the transformants from AJ12036 strain and YDK010 strain, respectively.

The strains grown overnight on the CM2S agar medium comprising 25 mg/l of kanamycin at 30° C. were inoculated into large tubes containing 4 ml of MMTG medium (Glucose 60 g/L, MgSO$_4$.7H$_2$O 1 g/L, MnSO$_4$.4H$_2$O 1 g/L, FeSO$_4$.7H$_2$O 1 g/L, (NH$_4$)$_2$SO$_4$ 30 g/L, KH$_2$PO$_4$ 1.5 g/L, VB1.HCl 450 Biotin 450 μg/L, DL-Met 0.15 g/L, pH 7.5) supplemented with 5% CaCO$_3$ and 25 μg/ml kanamycin, for 3 days at 30° C.

TABLE 3

The amount of extracellularly produced protransglutaminase by the mutant strains

| Producing Strain | Protransglutaminase |
|---|---|
| ATCC13869/pPKSPTG1 | 235 mg/L |
| AJ12036/pPKSPTG1 | 680 |
| YDK010/pPKSPTG1 | 700 |

TABLE 4

The amount of extracellularly produced SAMP45 by the mutant strains

| Producing Strain | SAMP45 |
|---|---|
| ATCC13869/pVSS1 | 9 mg/L |
| AJ12036/pVSS1 | 20 |
| YDK010/pVSS1 | 22 |

TABLE 5

The amount of extracellylarly produced svPEP by the mutant strains

| Producing Strain | svPEP |
|---|---|
| ATCC13869/pVSSSP1 | 50 mg/L |
| AJ12036/pVSSSP1 | 130 |
| YDK010/pVSSSP1 | 150 |

TABLE 6

The amount of extracellularly produced hEGF by the mutant strains

| Producing Strain | hEGF |
|---|---|
| ATCC13869/pPSEGF | 100 mg/L |
| AJ12036/pPSEGF | 280 |
| YDK010/pPSEGF | 290 |

As can be seen in Table 3 to Table 6, the remarkable improvement in the amount of the production of SAMP45, svPEP and hEGF by changing the host from the wild type to the streptomycin resistant strain AJ12036. However, only a slight improvement in the amount of secretory production was observed by completely deleting the cell surface protein (PS2) gene from AJ12036 strain. The negative effect caused by the competitive inhibition of PS2 secretion on the secretion of protransglutaminase or hEGF was not significantly observed in these cases. However, the secretion of PS2 was not observed at all in the complete PS2 gene defective strain, which contributed to the reduction of undesired contaminated proteins in the culture medium. This is a merit during the purification of protransglutaminase or hEGF.

Example 10

Effective Factors in Culturing on the Secretion of Protransglutaminase

The transformant obtained by transforming *Corinebacterium glutamicum* YDK010 strain with the previously described pPKSPTG1 was used for estimating the culture condition for the secretory production of protransglutaminase.

The strain grown overnight on the CM2S agar medium comprising 25 mg/l of kanamycin at 30° C. were inoculated into 500 ml Sakaguchi flask containing 20 ml of CM2S liquid medium, and was cultured overnight at 30° C. This was used for seed culture.

The effects of adding $CaCl_2$ was estimated in S-type Jar containing MMTG liquid medium (Glucose 60 g/L, $MgSO_4 \cdot 7H_2O$ 1 g/L, $MnSO_4 \cdot 4H_2O$ 1 g/L, $FeSO_4 \cdot 7H_2O$ 1 g/L, $(NH_4)_2SO_4$ 30 g/L, $KH_2PO_4$ 1.5 g/L, VB1.HCl 450 μg/L, Biotin 450 μg/L, DL-Met 0.15 g/L, pH 7.5) as the basal medium supplemented with 25 μg/ml kanamycin. 300 ml medium was placed in the flask. The amount of seeding was 5% (15 ml) and the dissolved oxygen concentration was controlled at 3% or less. The culture was carried out at 30° C. for 3 days.

After the culturing, 10 μl of the culture supernatant was subjected to SDS-PAGE and Western blotting was carried out using the above-described anti-transglutaminase antibody according to the conventional method. The results showed the effect of adding calcium in that about 1.3- to 2-fold increase in secretion amount was observed in $CaCl_2$ adding groups compared to the non-adding group.

TABLE 7

Effect of Calcium ion on secretory production of protransglutaminase

| CaCl2 (g/L) | Accumulation of protransglutaminase (mg/L) | Relative ratio |
|---|---|---|
| 0 | 460 | 1 |
| 0.25 | 610 | 1.3 |
| 0.5 | 790 | 1.7 |
| 1.0 | 810 | 1.8 |
| 2.0 | 930 | 2.0 |

The conditions for aeration and stirring were further studied using the MMTG medium containing 0.2 g/L $CaCl_2$, which revealed that the better results were obtained by controlling the dissolved oxygen concentration at 3% which is the measuring limit, or less (Table 8).

TABLE 8

Effect of the concentration of dissolved oxygen on the secretory production of protransglutaminase

| Dissolve oxygen concentration | Accumulation of protransglutaminase (mg/L) | Relative ratio |
|---|---|---|
| Below 3% | 930 | 1.43 |
| Controlling at 3% | 810 | 1.25 |
| Controlling at 5% | 650 | 1 |

According to the present invention, useful proteins, for example, heterologous proteins such as transglutaminase or human epidermal growth factor, can be produced in a large amount and can be efficiently extracellularly secreted (secreto-production) by coryneform bacteria. The protein produced according to the methods of the present invention are secreted into the culture medium, which make it possible to easily recover the protein from the culture media on a large scale using appropriate known methods.

Each of the aforementioned documents, as well as the foreign priority document, Japan 2001-98808, filed Mar. 30, 2001, are hereby incorporated by reference.

What is claimed is:

1. A method for producing a heterologous protein comprising
   A) culturing a *Corynebacterium glutamicum* AJ12036 (FERM BP-734) bacterium or mutant thereof having a genetic expression construct comprising a nucleic acid sequence encoding a signal peptide region from a coryneform bacterium which is downstream of a promoter sequence which functions in a coryneform bacterium, and a nucleic acid sequence encoding a heterologous protein which is downstream of said nucleic acid sequence encoding said signal peptide region, and
   B) recovering said heterologous protein, wherein said bacterium or mutant thereof is able to secrete the heterologous protein at least 2-fold higher than *Corynebacterium glutamicum* ATCC13869 having said genetic expression construct.

2. The method of claim 1, wherein said mutant does not produce a cell surface protein.

3. The method of claim 1, wherein said signal peptide region comprises a signal peptide of a cell surface protein from a coryneform bacterium.

4. The method of claim 1, wherein said signal peptide region comprises a signal peptide of a cell surface protein *Corynebacterium ammoniagenes*.

5. The method of claim 4, wherein said signal peptide comprises the amino acid sequence of SEQ ID NO: 3.

6. The method of claim 1, wherein said culturing of said bacterium or said mutant thereof is conducted in a medium containing at least 0.25 g/l (2.25 mM) of calcium ion.

7. The method of claim 1, wherein said culturing of said bacterium or said mutant thereof is conducted by controlling the dissolved oxygen concentration at 3% or less.

* * * * *